(12) United States Patent
Johnson

(10) Patent No.: US 12,407,748 B2
(45) Date of Patent: Sep. 2, 2025

(54) SYSTEM FOR STORING, PROCESSING, AND ACCESSING MEDICAL DATA

(71) Applicant: Tim Donald Johnson, Norwalk, IA (US)

(72) Inventor: Tim Donald Johnson, Norwalk, IA (US)

(73) Assignee: HEALTH IN TECH, INC., Norwalk, IA (US)

( * ) Notice: Subject to any disclaimer, the term of this patent is extended or adjusted under 35 U.S.C. 154(b) by 0 days.

(21) Appl. No.: 18/499,300

(22) Filed: Nov. 1, 2023

(65) Prior Publication Data

US 2024/0064193 A1 Feb. 22, 2024

Related U.S. Application Data

(63) Continuation-in-part of application No. 17/589,939, filed on Feb. 1, 2022, now Pat. No. 11,863,609, which is a continuation of application No. 16/936,684, filed on Jul. 23, 2020, now Pat. No. 11,277,497, application No. 18/499,300, filed on Nov. 1, 2023 is
(Continued)

(51) Int. Cl.
| | |
|---|---|
| *H04L 67/01* | (2022.01) |
| *G16H 10/60* | (2018.01) |
| *H04L 9/06* | (2006.01) |
| *H04L 67/133* | (2022.01) |

(52) U.S. Cl.
CPC ............ *H04L 67/01* (2022.05); *G16H 10/60* (2018.01); *H04L 9/0637* (2013.01); *H04L 67/133* (2022.05)

(58) Field of Classification Search
CPC . H04L 2209/88; H04L 9/0637; H04L 9/3234; H04L 9/50; H04L 63/0853; H04L 63/101; H04L 63/12; H04L 67/01; H04L 67/133; G16H 10/60; G16H 10/65
See application file for complete search history.

(56) References Cited

U.S. PATENT DOCUMENTS 10,586,617 B1 * 3/2020 McNair .................. G16H 50/30
11,277,497 B2    3/2022 Johnson
(Continued)

OTHER PUBLICATIONS

Microsoft. learn.microsoft.com. https://learn.microsoft.com/en-us/previous-versions/windows/it-pro/windows-10. (Year: 2017).*
(Continued)

*Primary Examiner* — John M MacIlwinen
(74) *Attorney, Agent, or Firm* — Christopher A. Proskey; BrownWinick Law Firm

(57) ABSTRACT

A system is disclosed for storage, processing, and accessing of data. The system includes a front end system and a back end system communicatively connected to the front end system. A front end system is configured to provide one or more user interfaces configured to store, process, and access data in a first data server, in response to user input, by sending messages to the back end system. The back end system includes the first data server and one or more processing servers. The one or more processing servers are configured to process messages received from the front end system by accessing in the first data server to perform one or more operations specified by the messages.

17 Claims, 17 Drawing Sheets

Related U.S. Application Data a continuation-in-part of application No. 18/103,067, filed on Jan. 30, 2023.

(60) Provisional application No. 62/879,876, filed on Jul. 29, 2019, provisional application No. 63/305,328, filed on Feb. 1, 2022.

(56) References Cited

U.S. PATENT DOCUMENTS

| | | | | |
|---|---|---|---|---|
| 11,863,609 | B2* | 1/2024 | Johnson | H04L 63/0892 |
| 2003/0236747 | A1* | 12/2003 | Sager | G06Q 20/357 |
| | | | | 705/40 |
| 2004/0030704 | A1 | 2/2004 | Stefanchik | |
| 2004/0103062 | A1 | 5/2004 | Wood | |
| 2005/0182774 | A1 | 8/2005 | Weir | |
| 2006/0053296 | A1 | 3/2006 | Busboom | |
| 2006/0200745 | A1 | 9/2006 | Furmanski | |
| 2006/0230286 | A1 | 10/2006 | Kitada | |
| 2007/0027715 | A1 | 2/2007 | Gropper | |
| 2008/0120133 | A1 | 5/2008 | Krishnaswami | |
| 2010/0241458 | A1 | 9/2010 | Hasan | |
| 2013/0061303 | A1* | 3/2013 | Hart | G06F 21/33 |
| | | | | 726/6 |
| 2013/0237152 | A1* | 9/2013 | Taggar | H04B 5/00 |
| | | | | 455/41.1 |
| 2013/0304510 | A1 | 11/2013 | Chen | |
| 2014/0200909 | A1 | 7/2014 | Felix | |
| 2014/0236635 | A1 | 8/2014 | Liberty | |
| 2015/0058145 | A1* | 2/2015 | Luciani | G06Q 20/3274 |
| | | | | 705/17 |
| 2020/0034850 | A1* | 1/2020 | Weiss | H04L 9/3271 |
| 2020/0366697 | A1 | 11/2020 | Vittal | |
| 2023/0245244 | A1 | 8/2023 | Johnson | |

OTHER PUBLICATIONS

Spiceworks. "How to delete user files after the user logs off the computer?" https://community.spiceworks.com/t/how-to-delete-user-files-after-the-user-logs-off-the-computer/145075. (Year: 2012).*

Wankhede, Deveshree, et al. "NFC based patient real time identification system." (Year: 2018).*

Alliance, Smart Card. "Smart Card Technology in US Healthcare: Frequently Asked Questions." Estados Unidos. (Year: 2012).*

Mashable. "A wristband with your medical records could be a life-saver in emergencies". https://mashable.com/article/wrixo-wristband. (Year: 2017).*

A. Azaria, A. Ekblaw, T. Vierira and A. Lippman, "MedRec: Using Blockchain for Medical Data Access and Permission Management", 2016 2nd International Conference on Open and Big Data (OBD), pp. 25-30 (Year: 2016).

P, Saint-Andre and L. Stout. "XEP-0234: Jingle File Transfer". Version 0.19.1, Jun. 18, 2019, pp. 1026 (Year: 2019).

* cited by examiner

SYSTEM FOR STORING, PROCESSING, AND ACCESSING MEDICAL DATA

CROSS REFERENCE TO RELATED APPLICATION

This application is a continuation-in-part of U.S. patent application Ser. No. 17/589,939 filed on Feb. 1, 2022 and titled "SYSTEM FOR STORING, PROCESSING, AND ACCESSING MEDICAL DATA", which is a continuation of U.S. patent application Ser. No. 16/936,684 filed on Jul. 23, 2020 and titled "SYSTEM FOR STORING, PROCESSING, AND ACCESSING MEDICAL DATA", which claims benefit of U.S. Provisional Patent Application No. 62/879,876 which was filed on Jul. 29, 2019, the entirety of each is hereby fully incorporated by reference herein.

This application is also a continuation-in-part of U.S. patent application Ser. No. 18/103,067 filed Jan. 30, 2023 and titled "SYSTEM AND METHOD FOR UNDERWRITING BENEFIT SYSTEMS COVERAGE APPLICATIONS", which claims benefit from U.S. Provisional Application No. 63/305,328 filed Feb. 1, 2022 and titled SYSTEM FOR STORING, PROCESSING, AND ACCESSING MEDICAL DATA, the entirety of each is fully incorporated by reference herein.

FIELD OF THE DISCLOSURE

This disclosure relates generally to data networking and processing. More specifically, and without limitation, this disclosure is directed to systems and methods for storing managing medical data and transactions.

OVERVIEW OF THE DISCLOSURE

Costs of healthcare in the United States continue to increase and are reaching unsustainable levels. Several healthcare industry analysis point to the fact that this is unsustainable, and something must be done to reverse the trend. Many attempts have indeed been made to rein in costs, however intended results always seem to not follow, or when they do, they are not long lasting. Contributing to high costs are inefficiencies related to the exchange, storage, and processing of transactions and other data across non-uniform and/or incompatible systems used by primary parties involved in the medical industry (e.g., healthcare providers, employer groups, third party administrators (TPAs), insurance (stop loss) companies).

Therefore, for all the reasons stated above, and the reasons stated below, there is a need in the art to improve storage, processing, and access to data and transactions related to medical services. It is an object of the disclosure to provide a system for storing, processing, and assessing data related to medical services.

Another object of the disclosure is to provide a system that is interoperable with third party systems.

Yet another object of the disclosure is to provide a system that facilitates transparency, security and verifiability of data.

Another object of the disclosure is to provide a system that improves efficiency in storage and processing of data and transactions.

Yet another object of the disclosure is to provide a system that utilizes a smart card to facilitate identification, authentication, and approvals.

Another object of the disclosure is to provide a system that is strong, robust, durable, and fault tolerant.

Yet another object of the disclosure is to provide a system that can be used in many applications.

Another object of the disclosure is to provide a system that provides unique functionality.

Yet another object of the disclosure is to provide a system that facilitates fast processing of data and transactions.

Another object of the disclosure is to provide a system that is scalable.

Yet another object of the disclosure is to provide a system that is distributed.

Another object of the disclosure is to provide a system that is easy and intuitive to use.

Yet another object of the disclosure is to provide a system that saves time.

Another object of the disclosure is to provide a system that improves a user experience.

These and other objects, features, or advantages of the disclosure will become apparent from the specification, figures and claims.

SUMMARY OF THE DISCLOSURE

Figure 1:
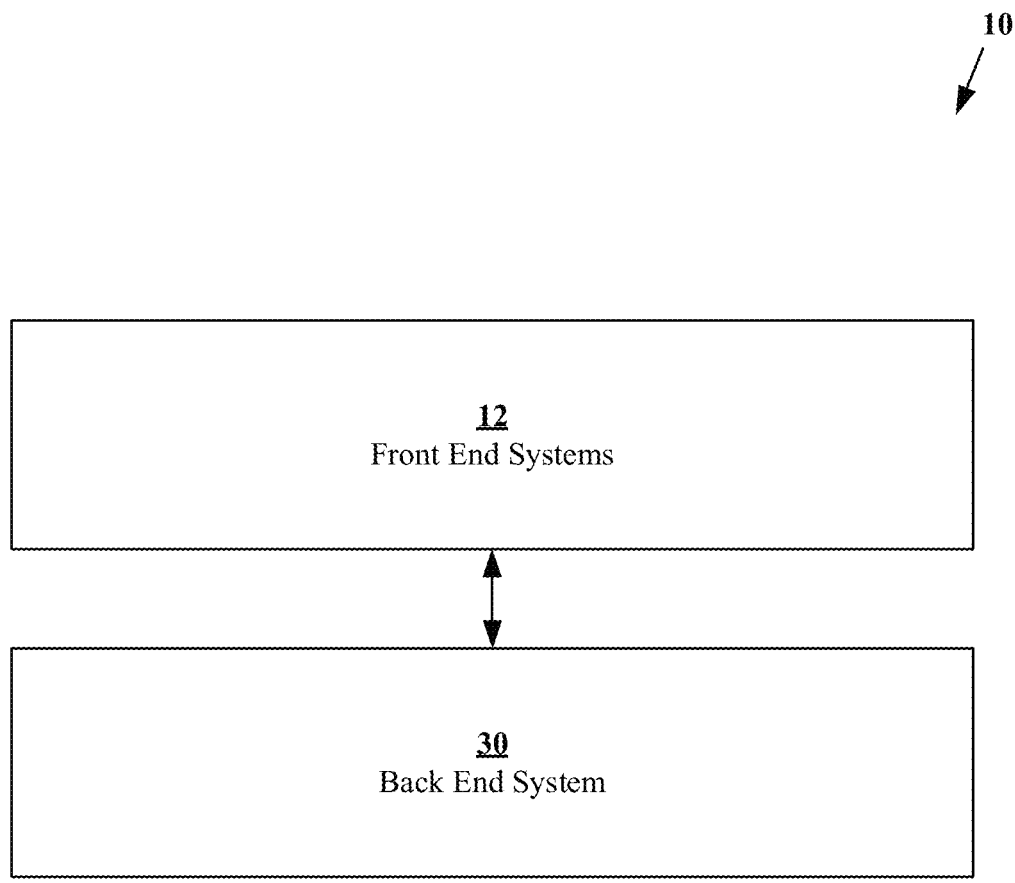
FIG. 1 shows a diagram of a system configured for storing, processing, and/or accessing data, consistent with one or more embodiments.
Figure 2:
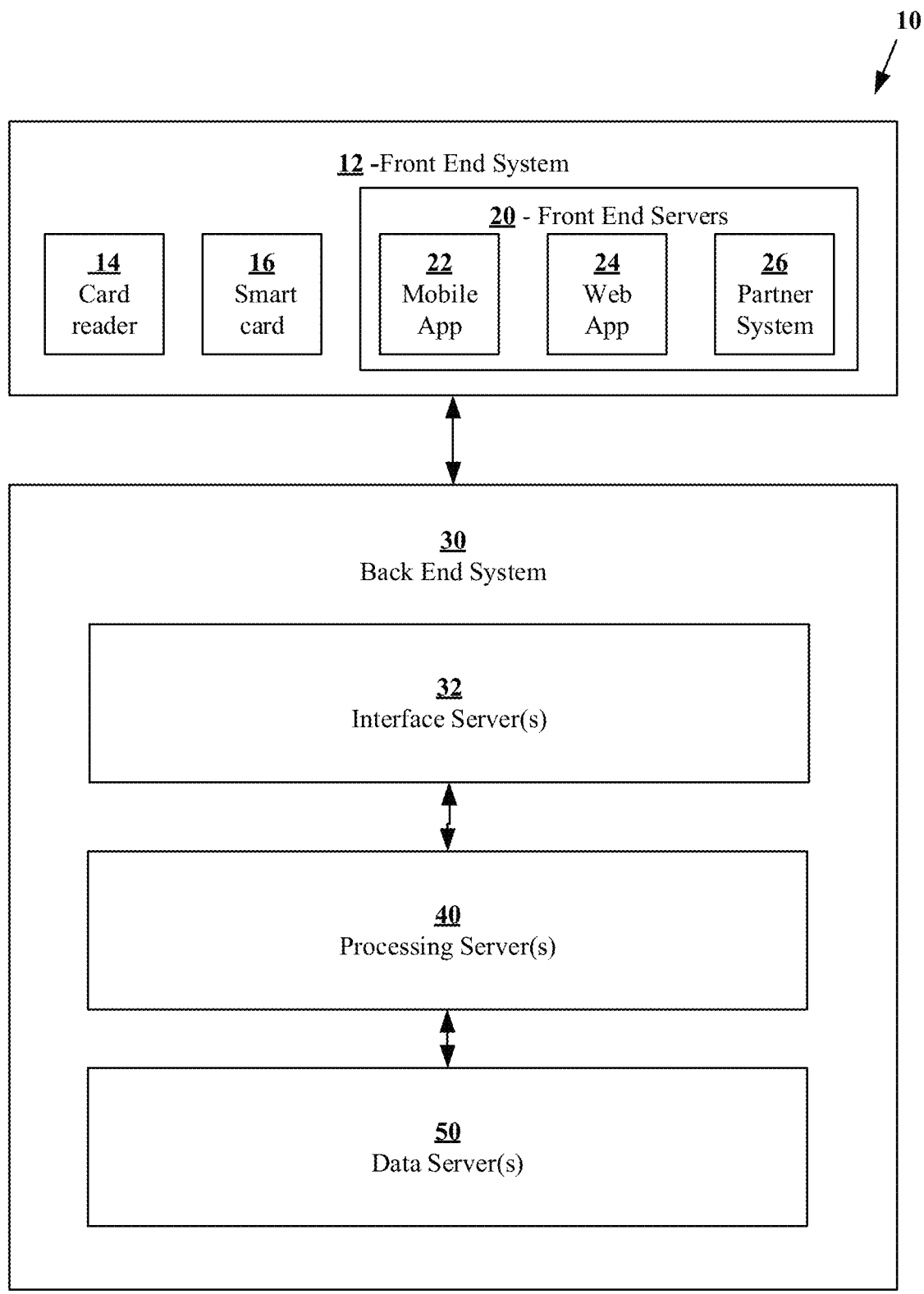
FIG. 2 shows a diagram of the system shown in FIG. 1; the diagram showing example implementations of front end system(s) and back end server(s), consistent with one or more embodiments.
Figure 3:
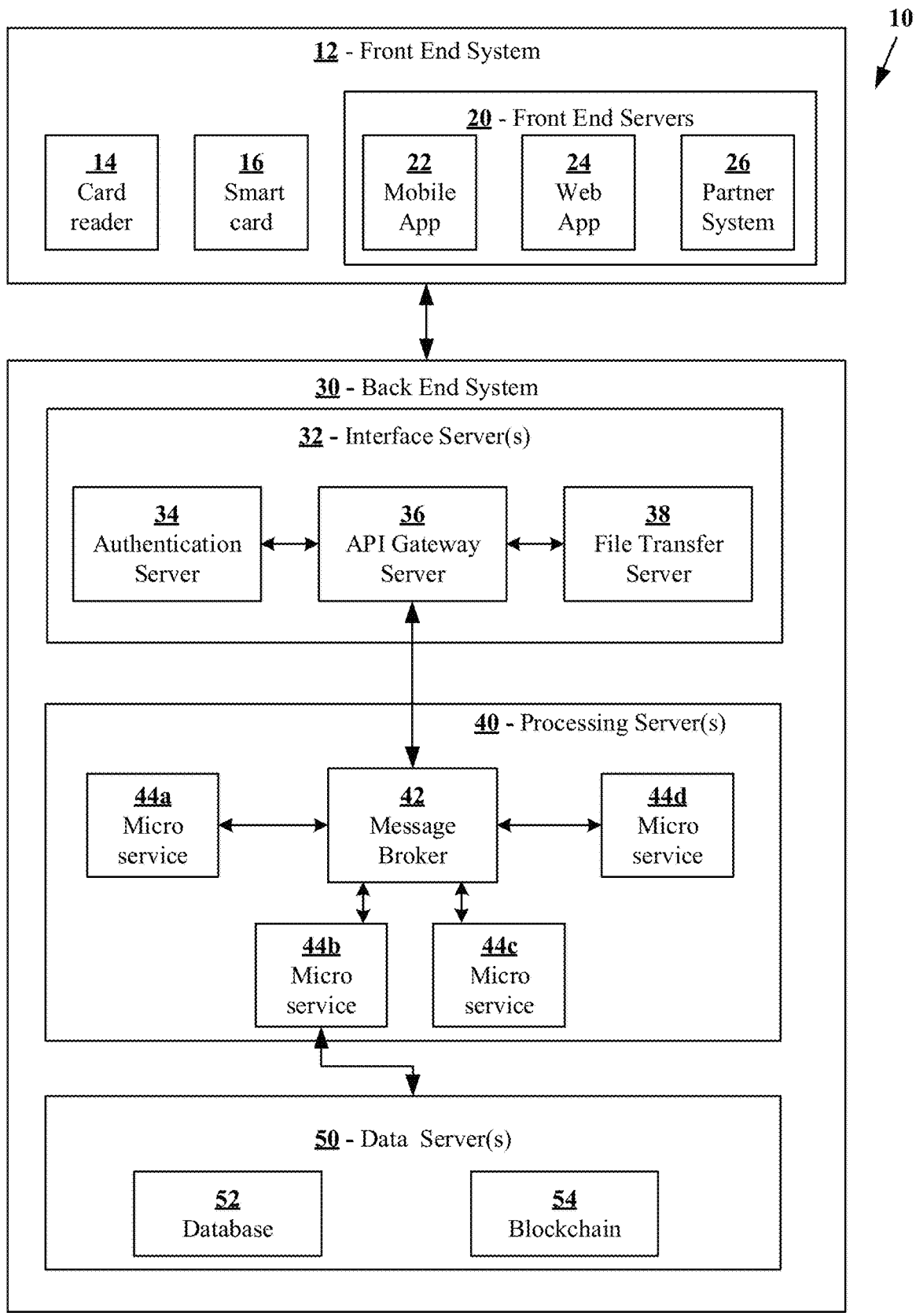
FIG. 3 shows a diagram of the system shown in FIG. 2; the diagram showing example implementations of interface server(s), processing server(s), and data server(s), consistent with one or more embodiments.
Figure 4:
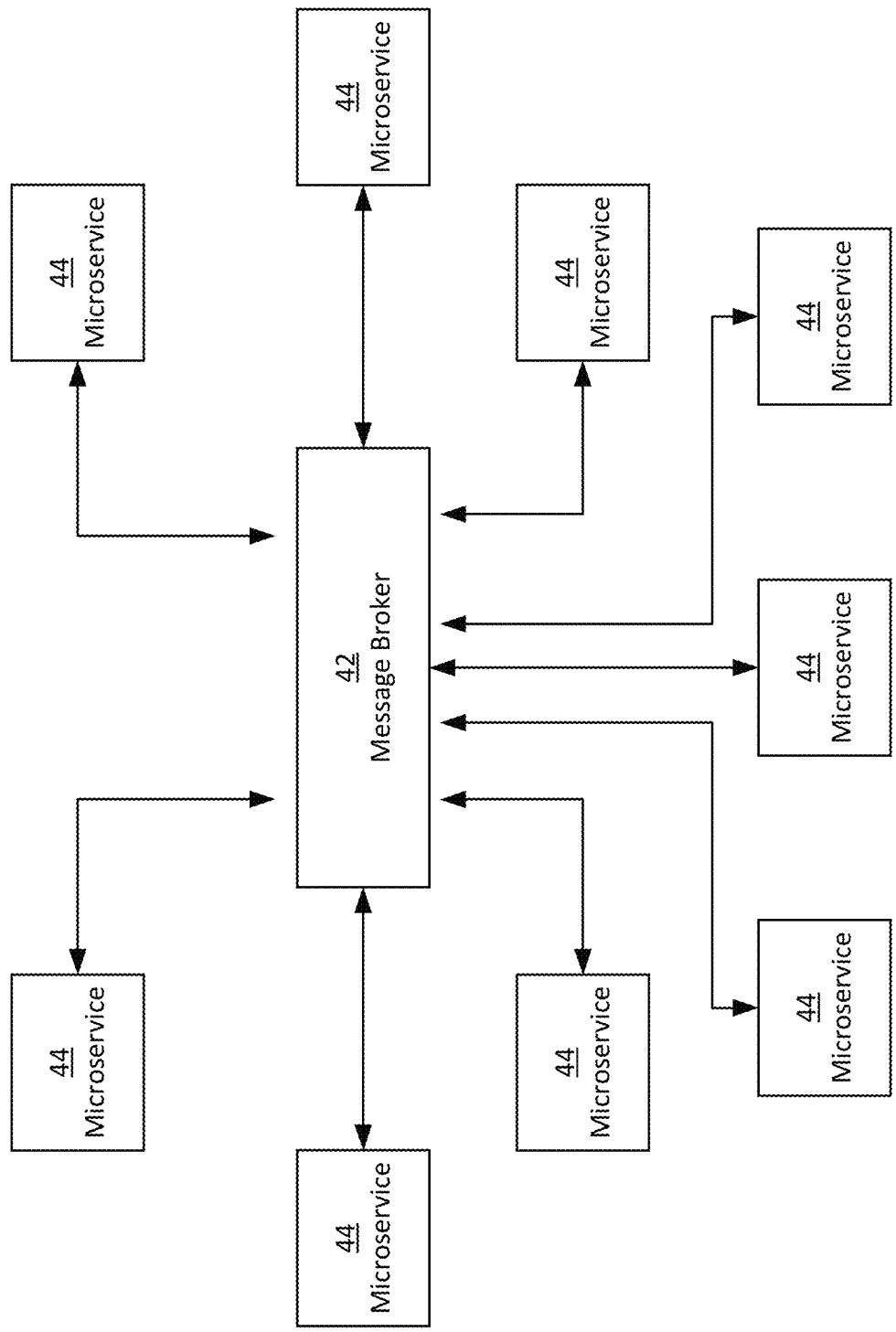
FIG. 4 shows a diagram of a processing server arrangement, consistent with one or more embodiments.

In one or more embodiments, a system is provided for storage, processing, and accessing of data. The system includes a front end system and a back end system communicatively connected to the front end system. The front end system includes one or more front end servers. The back end system includes a first data server. The one or more front end servers are configured to provide one or more user interfaces configured to store, process, and access data in the first data server, in response to user input, by sending messages to the back end system. The back end system includes one or more processing servers communicatively connected to the first data server. The one or more processing servers are configured to process messages received from the front end system by accessing in the first data server to perform one or more operations specified by the messages. The back end system also includes a second data server configured and arranged to maintain a record of changes made to data in the first data server by the one or more processing servers in a blockchain.

In one or more embodiments, the front end system includes a reader device configured to communicate with a smart card of a patient and the back end system to authenticate the smart card with the back end system. In response to authenticating the smart card, the reader device sends one or more messages to the back end system to retrieve the medical data of the patient from the first data server. The reader device is configured to display the retrieved medical data of the patient to the medical provider.

In one or more embodiments, the back end system includes one or more interface servers configured to operates as a gateway between the front end system, and the one or more processing servers.

In one or more implementations, the one or more interface servers includes an application program interface (API) server. The API server is configured to: receive the messages from the front end system; attempt to authenticate the received messages; forward ones of the authenticated messages that pass authentication to the one or more processing servers; and discard ones of the authenticated messages that fail authentication. In one or more implementations, the one or more interface servers includes an authentication server to perform the authentication.

In one or more implementations, the one or more interface servers includes a file transfer server configured to receive files from at least one server of the front end system using a file transfer protocol. In response to receiving a file from the front end system, the file transfer server is configured and arranged to: determine a sender of the file; retrieve a file format corresponding to the sender from a memory; and submit the file to the API server as a message in response to determining the file complies with the retrieved file format.

In one or more embodiments, the messages include a plurality of different types of messages. The one or more processing servers are configured and arranged to provide a plurality of micro services, each being is configured to process a subset of the different types of messages. In one or more implementations, the plurality of micro services includes a first micro service configured to process messages requesting changes to health care plan portfolios. In one or more implementations, the plurality of micro services includes a second micro service configured to process messages requesting access to the first data server or the second data server. In one or more implementations, the plurality of micro services includes a third micro service configured to process messages requesting setup of a new group health care plan.

In one or more embodiments, the one or more processing servers includes a message broker. The messages broker includes respective queue for each of the plurality of micro services. The messages broker is configured and arranged to receive the messages from the front end system and place each message in the respective queue of the micro service configured to process the message. The message broker is also configured to forward the next message in a queue to the respective micro service, in response to the micro service becoming available. In one or more embodiments, the micro services are configured to send messages to other micro services by sending the messages to the message broker.

In one of more embodiments, the front end system includes one or more card readers. The back end system is configured to authenticate the users with smart cards using the one or more card readers.

DETAILED DESCRIPTION OF THE DISCLOSURE

In the following detailed description of the embodiments, reference is made to the accompanying drawings which form a part hereof, and in which is shown by way of illustration specific embodiments in which the disclosure may be practiced. The embodiments of the present disclosure described below are not intended to be exhaustive or to limit the disclosure to the precise forms in the following detailed description. Rather, the embodiments are chosen and described so that others skilled in the art may appreciate and understand the principles and practices of the present disclosure. It will be understood by those skilled in the art that various changes in form and details may be made without departing from the principles and scope of the invention. It is intended to cover various modifications and similar arrangements and procedures, and the scope of the appended claims therefore should be accorded the broadest interpretation so as to encompass all such modifications and similar arrangements and procedures. For instance, although aspects and features may be illustrated in or described with reference to certain figures or embodiments, it will be appreciated that features from one figure or embodiment may be combined with features of another figure or embodiment even though the combination is not explicitly shown or explicitly described as a combination. In the depicted embodiments, like reference numbers refer to like elements throughout the various drawings.

It should be understood that any advantages and/or improvements discussed herein may not be provided by various disclosed embodiments, or implementations thereof. The contemplated embodiments are not so limited and should not be interpreted as being restricted to embodiments which provide such advantages or improvements. Similarly, it should be understood that various embodiments may not address all or any objects of the disclosure or objects of the invention that may be described herein. The contemplated embodiments are not so limited and should not be interpreted as being restricted to embodiments which address such objects of the disclosure or invention. Furthermore, although some disclosed embodiments may be described relative to specific materials, embodiments are not limited to the specific materials or apparatuses but only to their specific characteristics and capabilities and other materials and apparatuses can be substituted as is well understood by those skilled in the art in view of the present disclosure.

It is to be understood that the terms such as "left, right, top, bottom, front, back, side, height, length, width, upper, lower, interior, exterior, inner, outer, and the like as may be used herein, merely describe points of reference and do not limit the present invention to any particular orientation or configuration.

As used herein, "and/or" includes all combinations of one or more of the associated listed items, such that "A and/or B" includes "A but not B," "B but not A," and "A as well as B," unless it is clearly indicated that only a single item, subgroup of items, or all items are present. The use of "etc." is defined as "et cetera" and indicates the inclusion of all other elements belonging to the same group of the preceding items, in any "and/or" combination(s).

As used herein, the singular forms "a," "an," and "the" are intended to include both the singular and plural forms, unless the language explicitly indicates otherwise. Indefinite articles like "a" and "an" introduce or refer to any modified term, both previously-introduced and not, while definite articles like "the" refer to a same previously-introduced term; as such, it is understood that "a" or "an" modify items that are permitted to be previously-introduced or new, while definite articles modify an item that is the same as immediately previously presented. It will be further understood that the terms "comprises," "comprising," "includes," and/or "including," when used herein, specify the presence of stated features, characteristics, steps, operations, elements, and/or components, but do not themselves preclude the presence or addition of one or more other features, characteristics, steps, operations, elements, components, and/or groups thereof, unless expressly indicated otherwise. For example, if an embodiment of a system is described at comprising an article, it is understood the system is not limited to a single instance of the article unless expressly indicated otherwise, even if elsewhere another embodiment of the system is described as comprising a plurality of articles.

It will be understood that when an element is referred to as being "connected," "coupled," "mated," "attached," "fixed," etc. to another element, it can be directly connected to the other element, and/or intervening elements may be present. In contrast, when an element is referred to as being "directly connected," "directly coupled," "directly engaged" etc. to another element, there are no intervening elements present. Other words used to describe the relationship between elements should be interpreted in a like fashion (e.g., "between" versus "directly between," "adjacent" versus "directly adjacent," "engaged" versus "directly engaged," etc.). Similarly, a term such as "operatively", such as when used as "operatively connected" or "operatively engaged" is to be interpreted as connected or engaged, respectively, in any manner that facilitates operation, which may include being directly connected, indirectly connected, electronically connected, wirelessly connected or connected by any other manner, method or means that facilitates desired operation. Similarly, a term such as "communicatively connected" includes all variations of information exchange and routing between two electronic devices, including intermediary devices, networks, etc., connected wirelessly or not. Similarly, "connected" or other similar language particularly for electronic components is intended to mean connected by any means, either directly or indirectly, wired and/or wirelessly, such that electricity and/or information may be transmitted between the components.

It will be understood that, although the ordinal terms "first," "second," etc. may be used herein to describe various elements, these elements should not be limited to any order by these terms unless specifically stated as such. These terms are used only to distinguish one element from another; where there are "second" or higher ordinals, there merely must be a number of elements, without necessarily any difference or other relationship. For example, a first element could be termed a second element, and, similarly, a second element could be termed a first element, without departing from the scope of example embodiments or methods.

Similarly, the structures and operations discussed herein may occur out of the order described and/or noted in the figures. For example, two operations and/or figures shown in succession may in fact be executed concurrently or may sometimes be executed in the reverse order, depending upon the functionality/acts involved. Similarly, individual operations within example methods described below may be executed repetitively, individually or sequentially, to provide looping or other series of operations aside from single operations described below. It should be presumed that any embodiment or method having features and functionality described below, in any workable combination, falls within the scope of example embodiments.

As used herein, various disclosed embodiments may be primarily described in the context of the health care and medical related services. However, the embodiments are not so limited. It is appreciated that the embodiments may be adapted for use in other applications which may be improved by the disclosed structures, arrangements and/or methods. The system is merely shown and described as being used in in the context of health care and medical related services for ease of description and as one of countless examples.

System 10:

With reference to the figures, a networked computing system 10 (or simply system 10) is presented. The system 10 is formed of any suitable design, arrangement, and circuitry and is configured to facilitate storing, processing, and accessing data related to medical services. In one or more arrangements, as shown in FIG. 1 for example, the system 10 includes a front end system 12 and one or more back end system 30 among other components. Front end system 12 and back end system 30 are communicatively connected over one or more data networks.

Front End System 12:

In one or more arrangements, system 10 includes a front end system 12. Front end system 12 is formed of any suitable design, arrangement, and circuitry and are configured to facilitate storage, processing, or access to data in back end system 30 by end users. In the arrangement shown, front end system 12 includes a number of front end servers 20, a card reader 14, and a smart card 16, among other components.

Card Reader 14 and Smart Card 16:

Card reader 14 and smart card 16 are formed of any suitable design, arrangement, and circuitry and are configured to facilitate exchanges of data between the smart card 16 and the card reader 14 and facilitate authentication of a card holder. In some various arrangements, for example, smart card 16 and the card reader 14 may be configured to communicate via direct electrical connection (e.g., when smart card 16 is inserted into card reader 14), wirelessly (e.g., using RFID), and/or any other communication method.

In one or more arrangements, smart card 16 includes a processing chip and a memory storing a secret key that may be used to authenticate the card holder (e.g., a symmetric or asymmetric key) with an authentication server. As an illustrative example, via the card reader 14, an authenticating entity may provide a challenge number to the smart card 16. The processing chip performs a mathematical function (e.g., encryption, decryption, etc.) that uses the challenge number and secret key as input. After computing, the smart card 16 communicates the result back to the authenticating entity. If the result matches the number expected by the authentication service, the smart card 16 is authenticated. However, embodiments are not so limited. Rather, as described in more detail with reference to authentication server 34, some various embodiments may utilize various processes and/or technologies to perform authentication using a smart card 16.

Front End Servers 20:

Front end servers 20 are formed of any suitable design, arrangement, and circuitry and are configured to provide an interface for end-users to communicate with back end system 30 to store, process, or access data stored therein. In the arrangement shown, as one example, front end servers 20 includes mobile applications 22, web servers providing web apps 24, and/or partner software systems 26 configured to communicate with back end system 30 over one or more data networks. In one or more arrangements, one or more front end servers 20 are configured to interface with card reader 14 to authenticate or obtaining other information from smart card 16. For example, a front end server 20 may be configured to authenticate a user and/or obtain user information to facilitate faster login and interaction with a user portal, while reducing user errors (e.g., due to mistyping). As another example, a front end server 20 may be configured to provide an electronic payment system that uses the smart card 16 as method of payment. For instance, in one or more arrangements, system 10 may be configured to debit from a healthcare savings account, bank account, or other payment system linked to the smart card 16 by a health plan member, thereby permitting the member to use the smart card 16 for payment of a copay.

In Operation:

As an illustrative example, the use of smart card 16 and card reader 14 in connection with front end servers 20 is thought to be particularly useful in the health care context, for example, to facilitate identification and authentication of health plan member seeking medical services and facilitate permitted access and exchanges of data related to the member and/or medical services.

Continuing with the example in the health care context, in one or more arrangements, the front end servers 20 may be configured to provide respective user interface (e.g., web portal, mobile apps, and/or computer program), to facilitate storage of, processing of, and/or access to data in back end system 30, for various groups of users including, for example: health care consumers (e.g., employers, employees/health plan members, and/or health plan member dependents), health care providers (e.g., hospitals, clinics, and/or physicians), and payers (e.g., insurance companies, third-party administrators, and/or stop loss carriers).

User interface for different groups of users may provide access to different data resources processes and/or functions provided by back end system 30. As an illustrative example, a front end server 20 may be configured to provide a user interface for a health care provider. In this example, the user interface may permit users to engage with the back end system 30 to perform a number of actions including but not limited to, for example, authenticating and verifying eligibility of health plan members; importing health plan information into provider systems; submitting pre-authorization requests for procedures; editing provider profile information, retrieving and viewing medical/drug history of a health plan member (if authorized by the health plan member); and/or storing medical records.

As another illustrative example, a front end server 20 may be configured to provide a user interface for health plan members. In this example, the user interface may permit members to engage with the back end system 30 to perform a number of actions including but not limited to, managing profile and dependent information, configuring multi-factor authentication, accessing of medical/drug history records, granting third parties access to medical/drug history records, managing prescriptions, and/or managing payment services.

As yet another illustrative example, a front end server 20 may be configured to provide a user interface for a third party administrator. In this example, the user interface may permit third party administrator employees to engage with the back end system 30 to perform a number of actions including but not limited to, onboarding groups for new health plans, collecting claims data, storing data, updating group data, updating employee data, and/or updating dependent data.

Back End System 30:

Turning now to back end system 30, in one or more arrangements, system 10 includes one or more back end system 30. Back end system 30 is formed of any suitable design, arrangement, and circuitry and are configured to store, process and access to data, in response to requests from users via front end system 12, and is further configured to authenticate and restrict user's ability to store, process, and/or access data based on permissions allocated for the user. In the arrangement shown, as one example, back end system 30 includes one or more interface servers 32, one or more processing servers 40, and one or more data servers 50, among other components. Interface servers 32, processing servers 40, and data servers 50 are communicatively connected over one or more data networks and/or data buses.

Interface Server(s) 32:

Interface server(s) 32 are formed of any suitable design, arrangement, and circuitry and is configured to operate as an interface for front end system 12 to access resources and/or functionality provided by back end system 30. In one arrangement shown, as one example, interface server(s) 32 include an authentication server 34, an API gateway server 36, and a file transfer server 38 communicatively connected over one or more data networks and/or data buses.

Authentication Server 34:

Authentication server 34 is formed of any suitable design, arrangement, and circuitry and is configured to authenticate users of front end system 12. In various embodiments, authentication server 34 is configured to authenticate users using one or more authentication techniques and/or protocols including but not limited to, for example: Password Authentication Protocols, Challenge-Handshake Authentication Protocol, Extensible Authentication Protocol, Terminal Access Controller Access-Control System protocols, Remote Authentication Dial-In User Service, Diameter, Kerberos, Authentication and Key Agreement, CAVE-based authentication, CRAM-MD5, Digest, Host Identity Protocol, LAN Manager, NT LAN Manager, Open ID protocol, Password-authenticated key agreement protocols, Protocol for Carrying Authentication for Network Access, Secure Remote Password protocol, RFID-Authentication Protocols, Woo Lam 92 (protocol), Security Assertion Markup Language, and/or any other known authentication protocol.

API Gateway Server 36:

API gateway server 36 is formed of any suitable design, arrangement, and circuitry and is configured to operate as an interface for communication of messages between interface servers 32 and processing servers 40. In one or more embodiments, messages may include various data including but not limited to, for example, requests for data from data servers 50, requests to store or modify data in data servers 50, and/or requests for performance of one or more functions provided by back end system 30 (e.g., functions performed by micro services 44).

Figure 5:
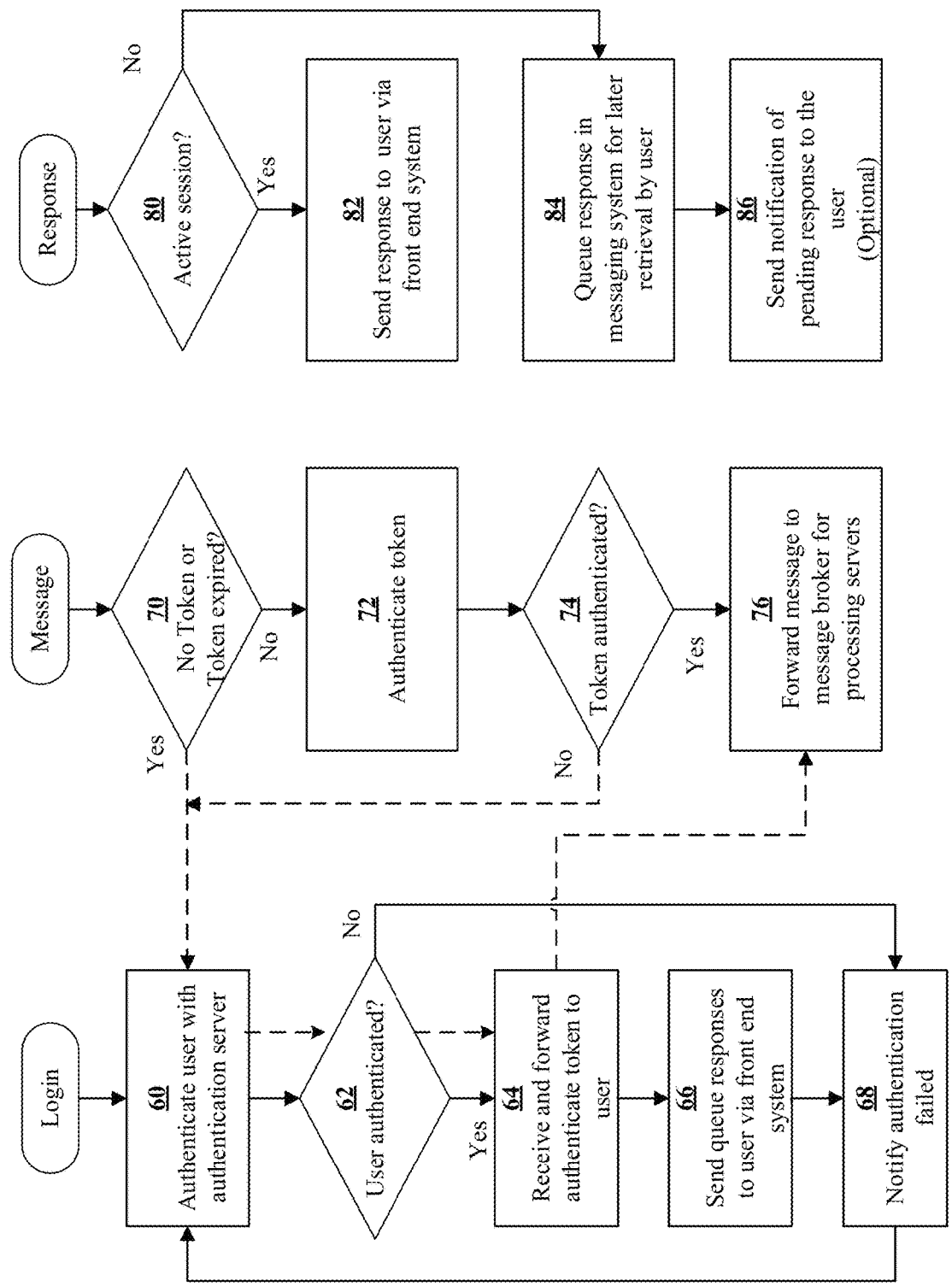
FIG. 5 shows a diagram of an example processes performed by API gateway server, consistent with one or more embodiments.
Figure 6:
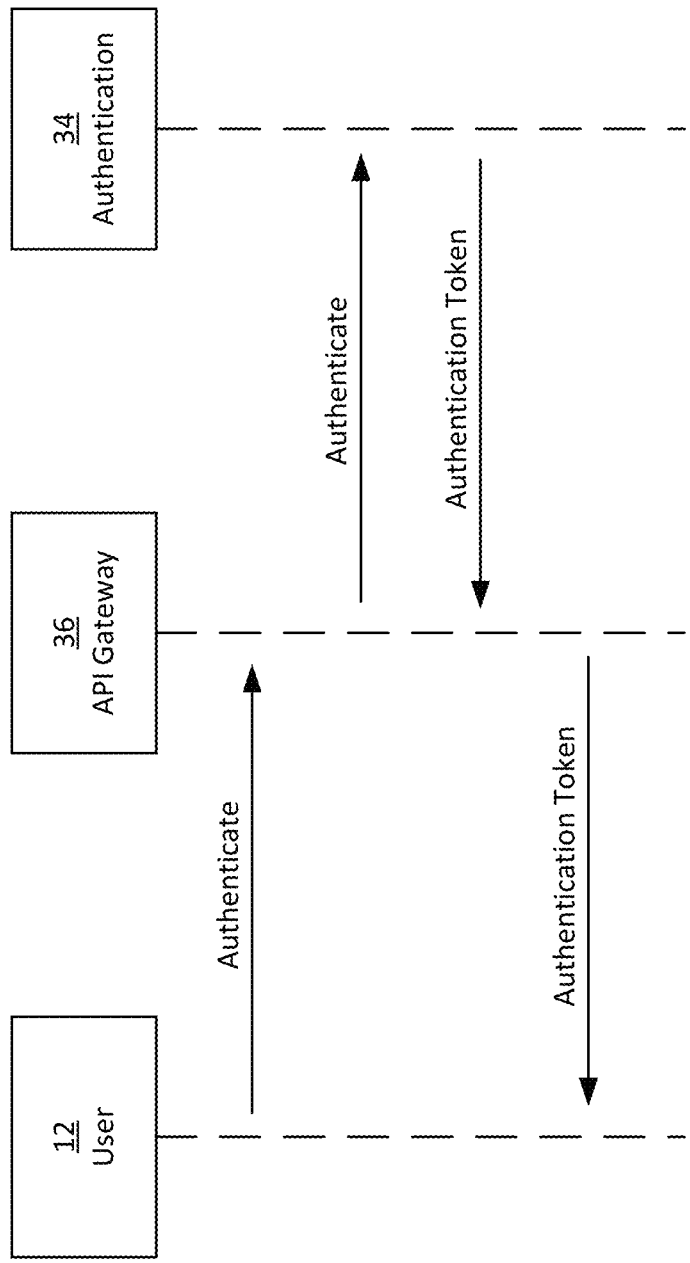
FIG. 6 shows a diagram of an example message flow for initial authentication of a user, consistent with one or more embodiments.
Figure 7:
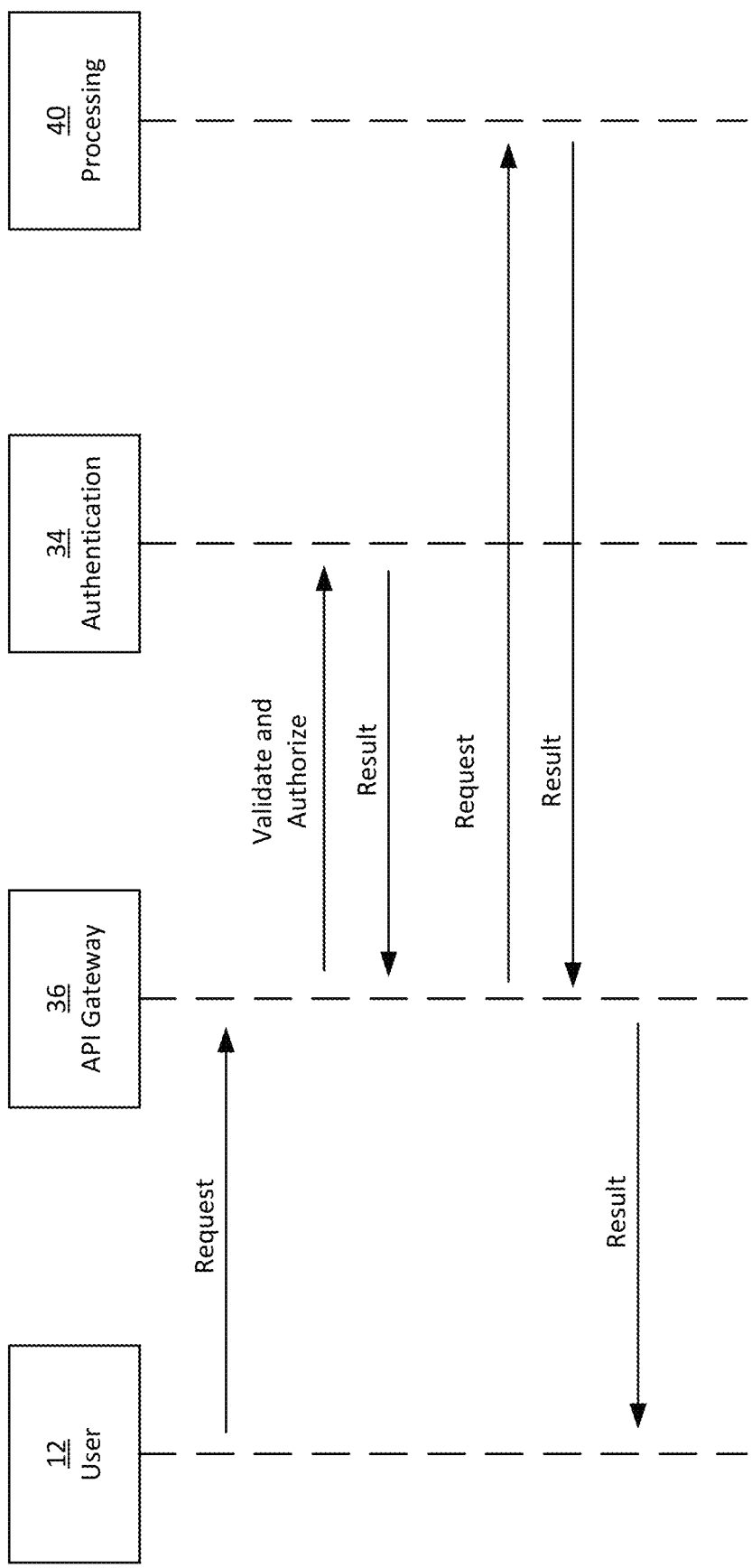
FIG. 7 shows a diagram of an example message flow for handling of messages by the API gateway server, consistent with one or more embodiments.

FIG. 5 shows a diagram of example processes performed by API gateway server 36, consistent with one or more embodiments. In response to a user attempting login to a front end system 12, API gateway server 36 authenticates the user with authentication server 34. If user is authenticated at decision block 62, an authentication token is received and forwarded to the user at block 64. Otherwise, the user is notified that authentication failed at block 68 and authentication is reattempted at block 60. The process continues in this manner until user is authenticated or user gives up. In some implementations, a user may be locked out of the system if authentication fails a number of times.

After the authentication token is forwarded to the user at block 64, any messages waiting for the user are sent to the user at block 66 via front end system 12. In this example, after authentication token is issued, the authentication token is used to authenticate messages subsequently submitted to API gateway server 36 by user. For ease of explanation, the example processes are described with reference to authentication tokens that remain valid for remainder of the user session. However, embodiments are not so limited. Rather, in some implementations, authentication tokens may remain valid for shorter or longer periods of time or even indefinitely.

In response to receiving a message from front end system 12, API gateway server 36 performs the process starting at decision block 70. If the received message includes an active token at decision block 70, the API gateway server 36 authenticates the authentication token with authentication server 34 at block 72. If token is successfully authenticated at decision block 76, API gateway server 36 forwards the message to message broker 42 of processing servers 40 at block 76.

If the received message does not include an authentication token or if the authentication token is expired at decision block 70 or if authentication of the token failed at decision block 74, the process proceeds to block 60 to authenticate or reauthenticate the sender or the message as previously described with reference to blocks 60, 62, 64, 66, and 68. If authentication is successful, the process proceeds to block 76 where API gateway server 36 forwards the message to message broker 42 of processing servers 40 for processing. Otherwise, the message is discarded.

As will be described in more detail with reference to processing servers 40, processing servers 40 may process messages received from API gateway server 36 in a stateless asynchronized manner, where response time is not guaranteed. Accordingly, it is possible that a user session may end before the message is processed and a response (e.g., requested data, report, or confirmation of performed action) is provided back to API gateway server 36.

In response to receiving a response from processing servers 40, API gateway server 36 performs the process starting at decision block 80. If a session for the sender that submitted the original message is active at decision block 80, API gateway server 36 sends the response to the user via front end system 12. If the user does not have an active session at decision block 80, the response is queued in a messaging system at block 84 for later retrieval by the user. If the user does have an active session at decision block 80, the response is sent at block 82 to the user via the front end system 12. Optionally, if the user does not have an active session at decision block 80 and the response is queued in a messaging system at block 84, a notification of the pending response can be sent to the user at block 86. In some implementations, API gateway server 36 may also send a notification (e.g., SMS, email, and/or push notification) that response is pending to the user.

File Transfer Server 38:

File transfer server 38 is formed of any suitable design, arrangement, and circuitry and is configured to receive data files from front end servers 20 for processing by back end system 30. File transfer server 38 may be used, for example, to enable partner software systems 26 that are not configured to communicate directly with API gateway server 36 to submit data files for processing by back end system 30. File transfer server 38 may be configured to receive files using one or more file transfer protocol including but not limited to, for example, SFTP, FTPS, ASS2, HTTPS, MFT, and/or any other known file transfer protocol.

Figure 8:
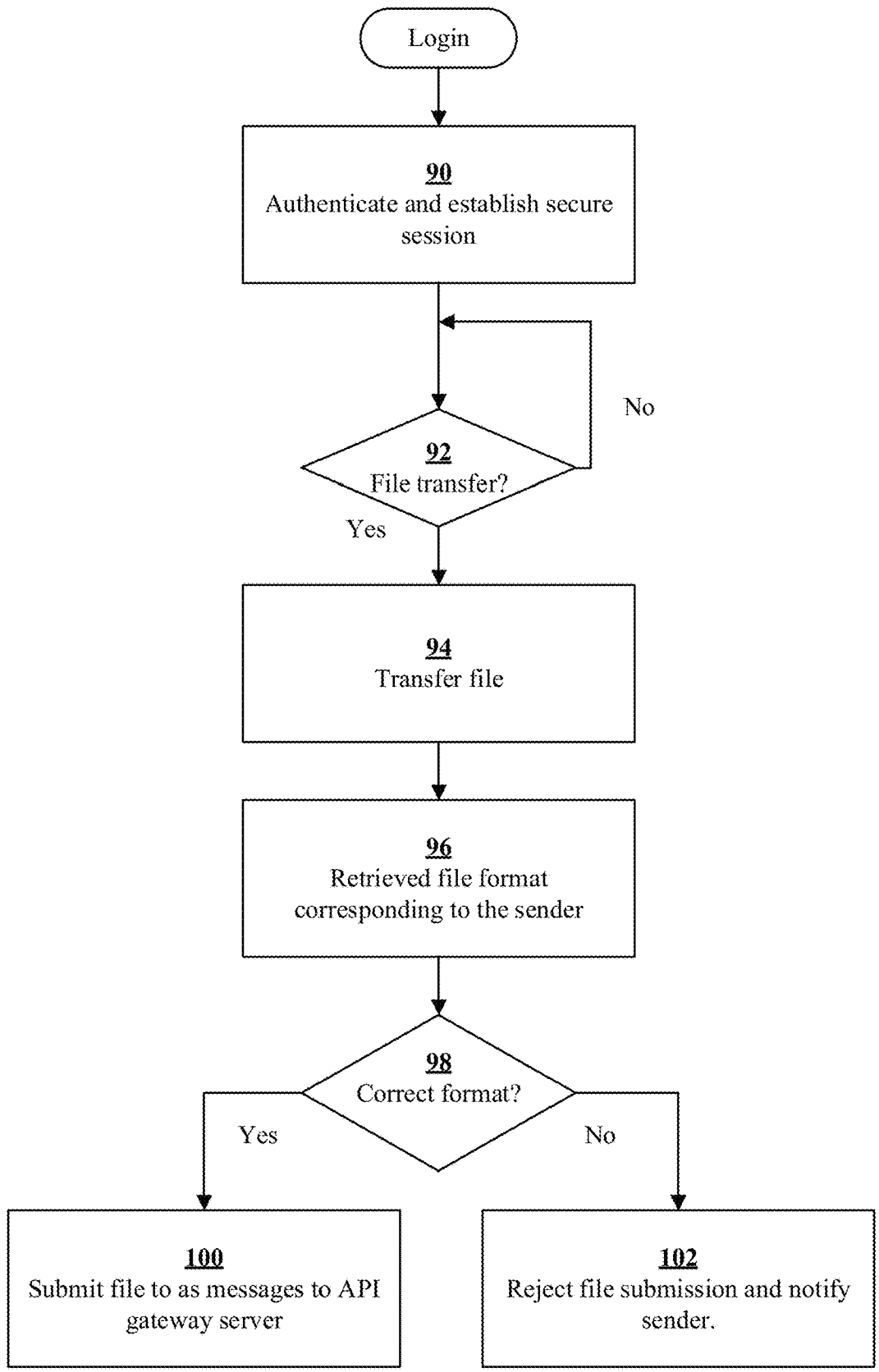
FIG. 8 shows a diagram of an example process performed by file transfer server, consistent with one or more embodiments.

FIG. 8 shows a diagram of an example process performed by file transfer server 38, consistent with one or more embodiments. In response to login request to file transfer server 38 (e.g., by a partner software 26), the user/system is authenticated, and a secure session is established at block 90. In this example, the file transfer server 38 waits at decision block 92 until a file transfer is requested. Once a transfer is requested, the file is transferred to the file transfer server 38 at block 94.

As previously noted, file transfer server 38 may be used in some situations to enable partner systems 26 that are not configured to communicate API gateway server 36 to submit files. Such partner systems may be configured to submit data files in their own unique file formats. To facilitate processing of partner format files, in one or more embodiments, back end system 30 is configured to store and use one or more agreed to formats previously provided by the partners. In this example process, file transfer server 38 is configured to check received files to ensure the files are in a format that can be processed by back end system 30. At block 96, file transfer server 38 retrieves a file format corresponding to the logged in sender (e.g., from a memory). If the file does not follow the retrieved format for the sender, at decision block 98, file transfer server 38 rejects the file submission and notifies the sender at block 102. If the file complies with the retrieved format, file transfer server 38 submits the file as a message to the API gateway server at block 100.

Processing Server(s) 40:

Processing server(s) 40 is formed of any suitable design, arrangement, and circuitry and is configured to process files and/or messages for the back end server to facilitate user access to resources and/or functionality provided by back end system 30. In an arrangement shown, as one example, processing server(s) 40 include a message broker 42 and a plurality of micro services 44.

Message Broker 42:

Message broker 42 is formed of any suitable design, arrangement, and circuitry and is configured to facilitate routing and communicating of messages and/or files to micro services 44 for processing. In an arrangement shown, as one example, message broker 42 is communicatively connected to micro services 44 and to API gateway server 36 via one or more data networks and/or data busses. In this example arrangement, message broker 42 is configured to operate as the primary channel for communicating messages/files to each micro service 44 for processing.

Figure 9:
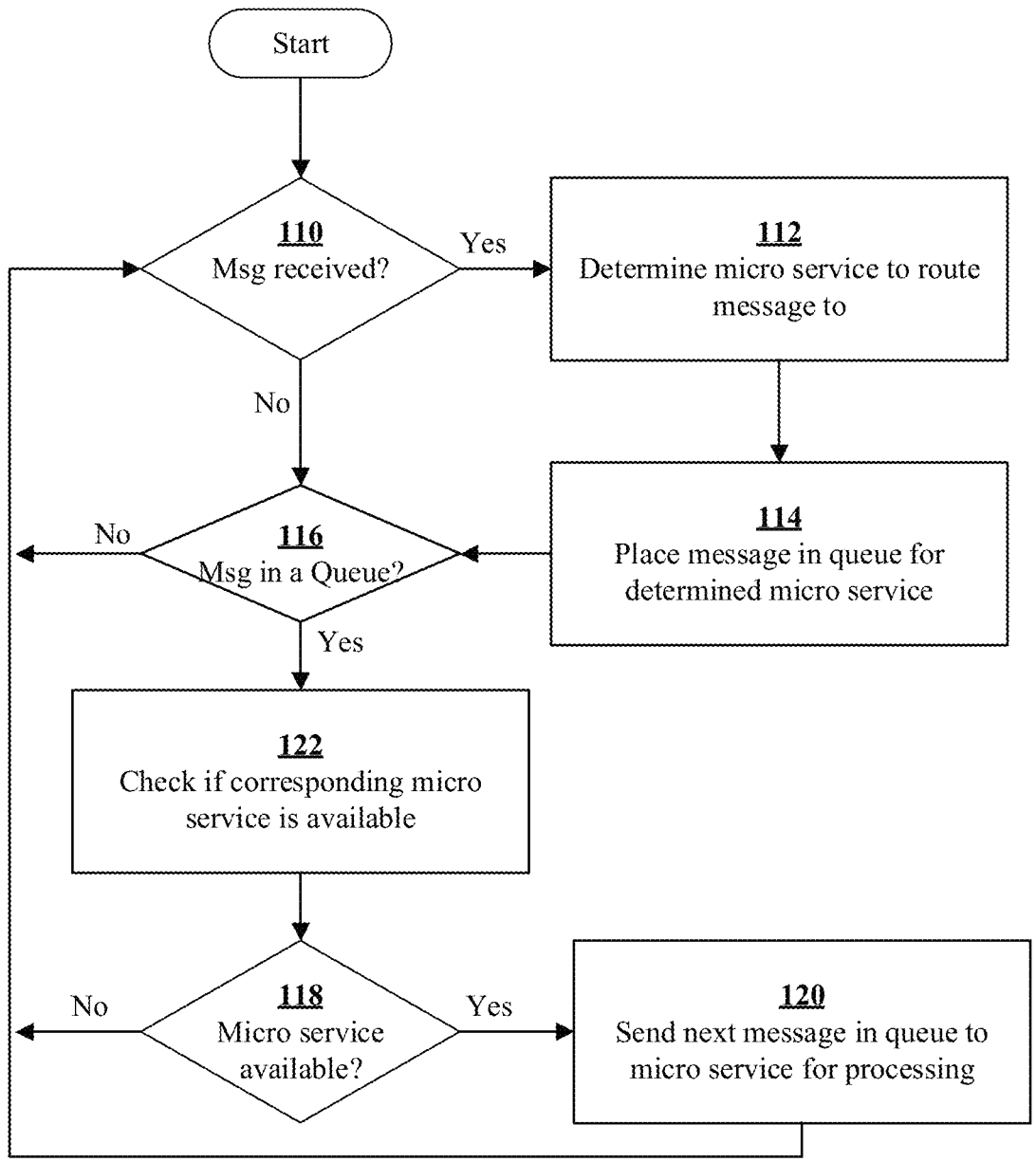
FIG. 9 shows a diagram of an example process performed by message broker, consistent with one or more embodiments.

In various embodiments, message broker 42 may perform routing and communicating messages using any suitable set of processes or tasks. FIG. 9 shows an example process that may be performed by message broker 42 for routing and communicating messages in one or more embodiments. In this example, process starts at decision block 110. If a message is received at decision block 110, message broker 42 determines the appropriate micro service 44 to route the message to at block 112. At block 114, message broker 42 places the message in a respective queue within message broker 42 for the determined micro service 44 and proceeds to decision block 116. At decision block 116, the message broker 42 checks messages queues. For any queue having a message pending, message broker 42 checks at block 122 to see if the corresponding micro service 44 is available. If the micro service 44 is available at decision block 118, message broker 42 sends the next message in the queue to the micro service 44 for processing at block 120. If the corresponding micro service(s) 44 for waiting messages is not available at decision block 118, or if no messages are waiting in queue at decision block 116, the process returns to decision block 110 and the example process is repeated.

Micro Services 44:

Micro Services 44 are formed of any suitable design, arrangement, and circuitry and are configured to process messages and/or data files to provide various resources and/or functionality to users. In various embodiments, processing servers 40 may include any number of micro services 44. In various embodiments, micro services 44 may also be configured to perform any number of different functions. In performing various functions, micro services 44 may perform functions autonomously and/or may generate messages to other micro services 44 to request performance of other functions.

In Operation:

For ease of explanation, and continuing with the example in the healthcare context, example arrangements are primarily discussed with reference to processing servers 40 having an arrangement of four example micro services 44: a portfolio management micro service 44a, a data access micro service 44b, a business management micro service 44c, and a file processing micro service 44d.

In this example arrangement, in one or more embodiments, portfolio management micro service 44a is configured to perform changes to health plan portfolio data. Portfolio data may include but is not limited to, for example, information, preferences, and/or transaction history for the employer, employee/member, and/or member dependents.

In this example arrangement, data access micro service 44b is communicatively connected to message broker 42 and data server 50. Data access micro service 44b is configured to perform operations to access data server 50 in response to requests received from interface servers 32 or other micro services 44.

In this example arrangement, business management micro service 44c is configured to perform a number of business related administrative tasks including but not limited to, for example, smart card manufacturing processes, notification and statement mailing, pre-authorization (case management) processes, health plan sales and quoting processes, etc.

In this example arrangement, file processing micro service 44d is configured to process files received and submitted by file transfer server 38. As an illustrative example, a third party administrator may submit a file for the sale of a new employer health plan. In processing the file, file processing micro service 44d may send one or more messages to portfolio management micro service 44a, via messages broker 42, to request creation of portfolio entries for the employer, employee/member, dependents, etc. File processing micro service 44d may also send one or more messages to business management micro service 44c, via messages broker 42, for example, to request generation of smart cards for new employee members and mailing of new member documents. In some scenarios, file processing micro service 44d may also send one or more messages to data access management micro service 44b, for example, to request information specified in the processed file. In processing the requests from file processing micro service 44d, portfolio management micro service 44a and business management micro service 44c may also generate and submit messages for other micro services 44 to the messages broker 42. For instance, portfolio management micro service 44a and business management micro service 44c may send messages to data access micro service 44b, via message broker 42, to read data from and/or write data to data servers 50.

While various components of system 10 may be primarily illustrated and described as separate components, embodiments are not so limited. Rather, it is understood that separate components may be combined and implemented together as a single component. Conversely, it is understood that a single component may be split and implemented by separate communicatively connected components. As an illustrative example, micro services 44a, 44b, 44c, and 44d may be implemented by respective computer servers or circuits, by respective computing resources (e.g., processors/cores and memory) in a shared computer server, and/or by respective processes/threads operating on shared computing resources.

Additionally or alternatively, in one or more embodiments, one or more micro services 44 may be implemented by a separate platform system. For example, business management micro service 44c may use a third party platform to one or more business related processes (e.g., smart card manufacturing, notification and statement mailing, pre-authorization (case management) processes, health plan sales and quoting processes.

Data Server(s) 50:

Data server(s) 50 are formed of any suitable design, arrangement, and circuitry and are configured to store data. In an arrangement shown, as one example, data server includes a database server 52 and a blockchain server 54.

In this example arrangement, database server 52 is configured to store all data for system 10. Continuing with the illustrative example in the healthcare context, data for the system 10 may include but is not limited to, for example, group and member data, medical history, billing transactions and records, pre-authorization requests, insurer information, provider information, service locations, and/or related other health care related records.

In this example arrangement, blockchain server 54 is configured to record a history of transactions and/or events in the system 10 a blockchain. Block chains utilize a self referencing data structure to store data as a series of blocks. Generally, each block includes contains a cryptographic reference (e.g., a hash) of the previous block, a timestamp, and a set of data. Once recorded, the data in any given block cannot be altered retroactively without alteration of all subsequent blocks. This arrangement makes blockchains extremely resistant to tampering or modification of data. Blockchains enable the traversal backwards in time across all previously recorded blocks to prove the validity of the data written therein. In the healthcare context, storing the history of transactions and/or events in a block chain can be used to increase transparency for plan members, providers, and payers. It is anticipated that increased transparency will improve the quality of care, improve efficiency, and reduce health care costs.

In some arrangements, block chain server 54 is a stand-alone block chain server. Alternatively, in some arrangements, block chain server 54 may be one node in a block chain network having redundant copies of the block chain distributed and synchronized across a plurality of nodes.

Figure 10:
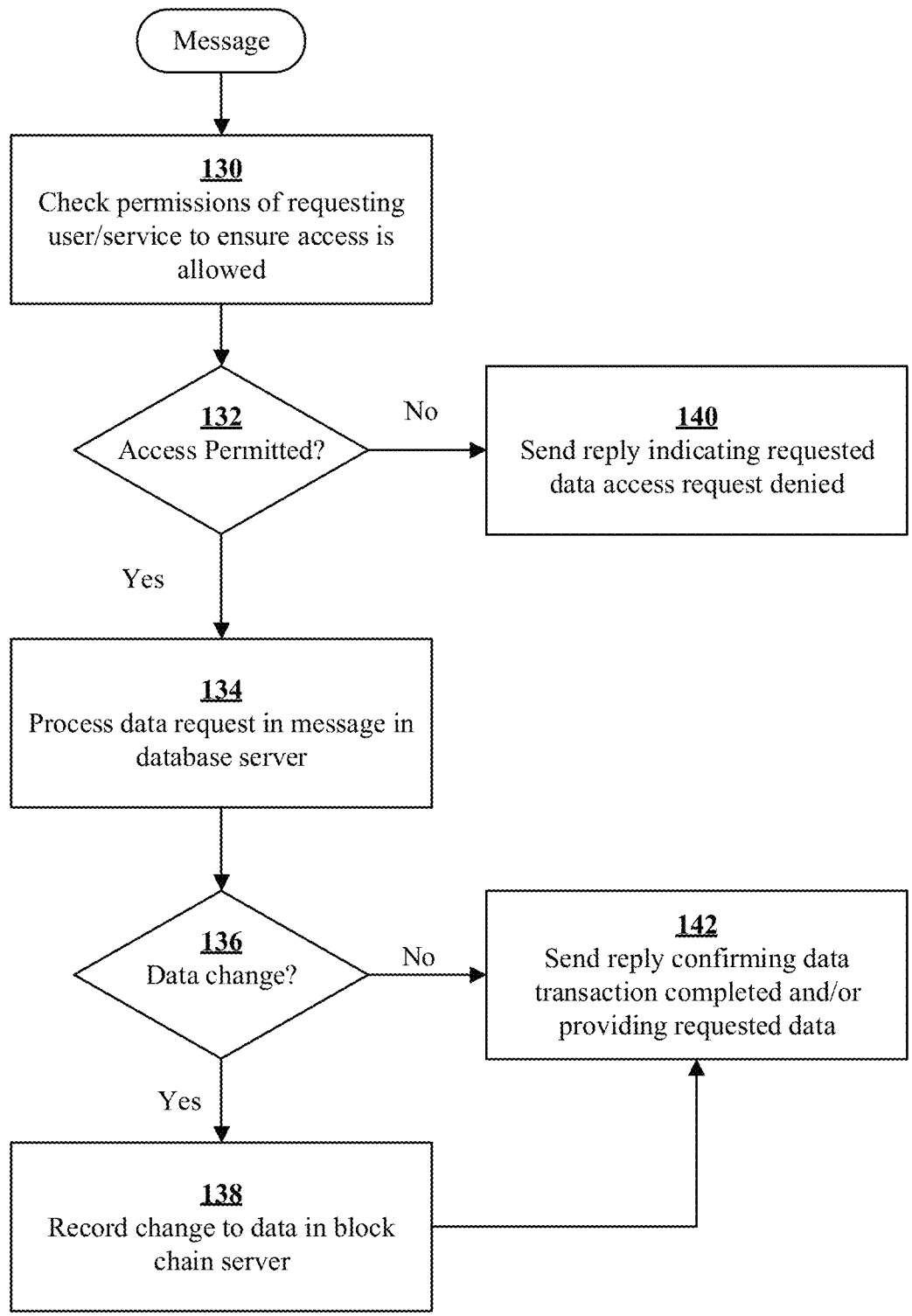
FIG. 10 shows a diagram of an example process performed by data servers, consistent with one or more embodiments.
Figure 11:
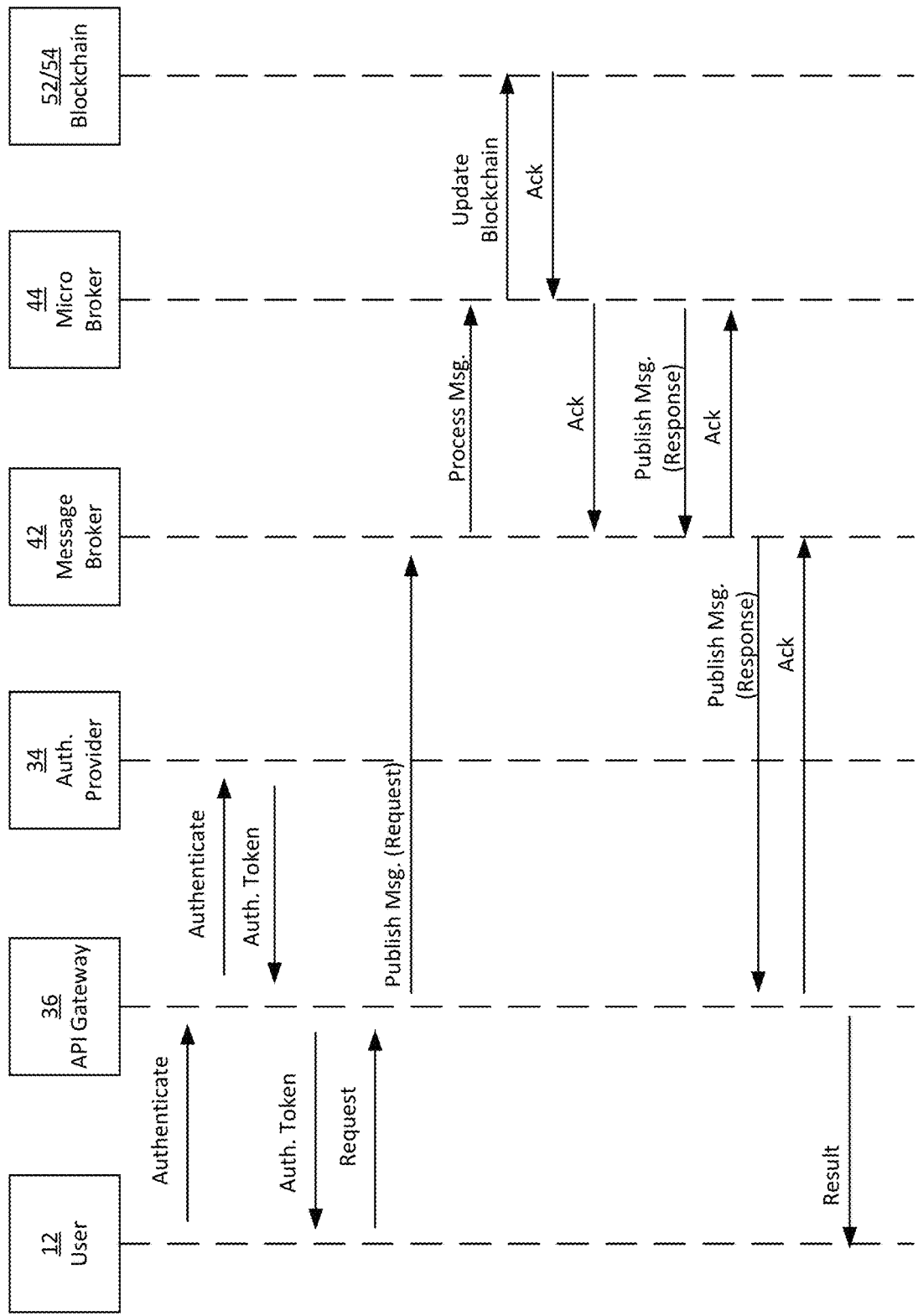
FIG. 11 shows a diagram of an example message flow, consistent with one or more embodiments.
Figure 12:
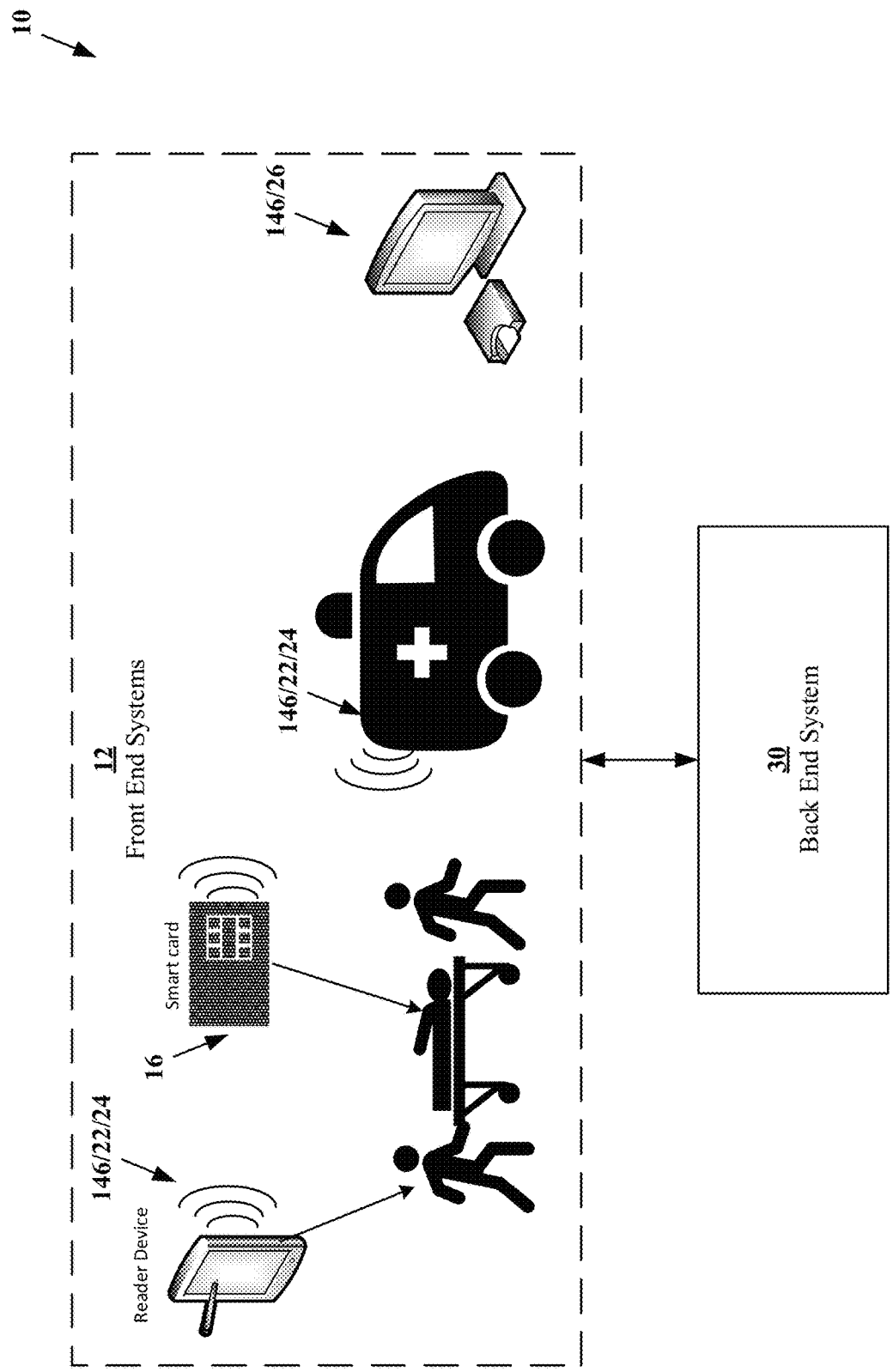
FIG. 12 shows a diagram of a system configured for providing a medical provider access to medical data of a patient, consistent with one or more embodiments.
Figure 13:
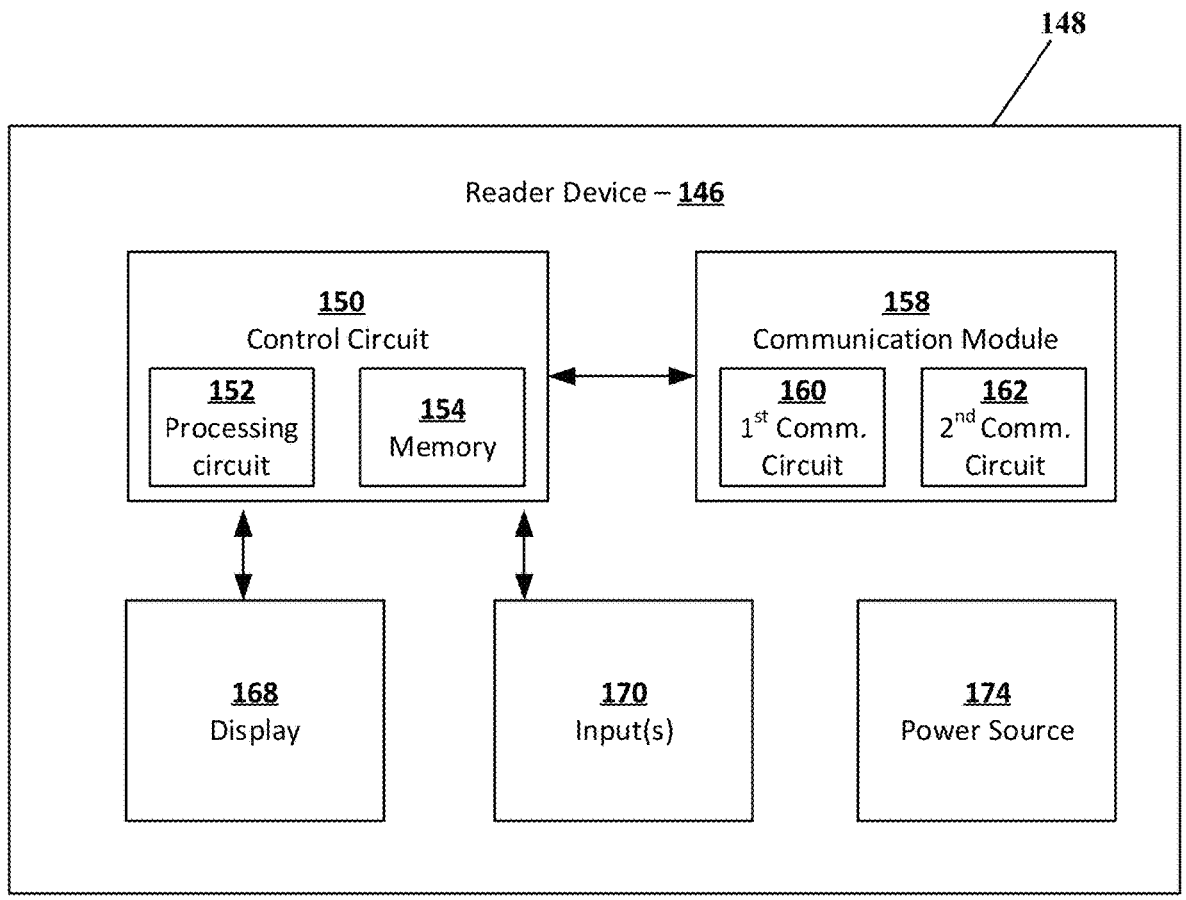
FIG. 13 shows a diagram of a reader device for retrieval and display of medical data of a patient, consistent with one or more embodiments.
Figure 14:
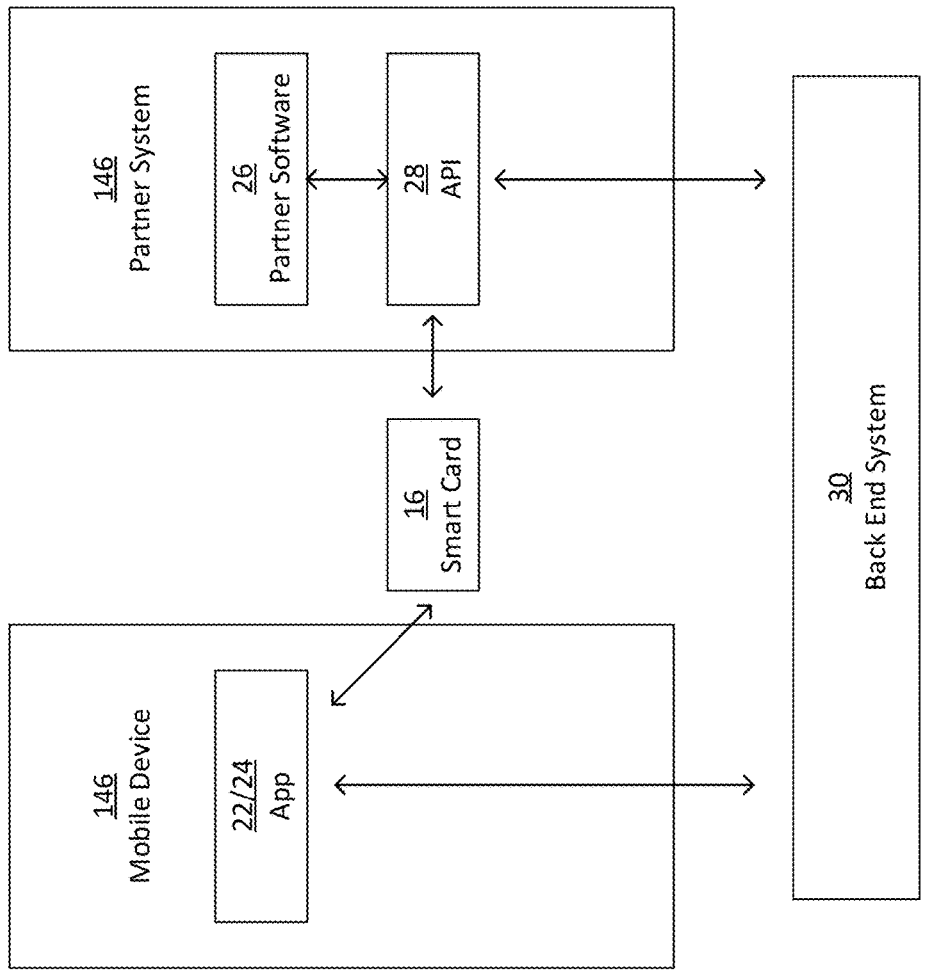
FIG. 14 shows a diagram of a system configured for providing a medical provider access to medical data of a patient, consistent with one or more embodiments.

FIG. 10 shows a diagram of an example process performed by data servers 50, consistent with one or more embodiments. In this example, in response to receiving a message, data servers 50 check permissions of the requesting user/service to ensure that the requested access is allowed. For example, in one or more implementations, permissions of the requesting user/service may be determined by examining an authentication token that is included with the message. For instance, in one or more implementations, the authentication token may indicate a permission level or an identifier from which permitted accesses may be determined (e.g., by looking up data resources to be accessed in a permissions table stored in a memory). In some various implementations, permission for access to different data resources may be specified for groups or categories of users (e.g., health care providers, third party administrators, etc.), for individual users, for categories of data resources, and/or for individual data resources.

Permissions of the requesting user or service is checked at process block 130. If it is determined that the requested data access is not permitted, at decision block 132, data servers 50 send a reply at block 140 indicating that the requested data access request is denied. Otherwise, database server 52 processes the data access request at block 134, indicated in the message, in database server 52.

In this example process, data servers 50 are configured to record data transactions in a blockchain only if the transaction changes data. Additionally or alternatively, in some embodiments, data servers 50 are configured to record data transactions in the blockchain that do not change data in database server 52. Recording data accesses that do not change data may be useful, for example, to ensure compliance with the Health insurance Portability and Accountability Act. If the processed data access request changes data in database server 52, decision block 136 directs the process to block 138, where blockchain server 54 records the data change in a blockchain. If the blockchain is a distributed blockchain, other nodes in the blockchain network are also updated at block 138.

After updating the blockchain at block 138, or if the data access transaction did not change the data, the process proceeds to block 142, where data servers 50 send a reply confirming that the data transaction indicated in the messages was completed and/or providing the requested data.

In Operation:

To facilitate understanding of the interoperation and communication between various components of system 10, some illustrative examples are provided that describe messages flow and operations performed in response to a user request.

Continuing with the example in the health care context, a health plan may be activated for a new member by a third party administrator submitting an eligibility file to system 10. In this example, the eligibility file may be submitted to file transfer server 38 by a front end server 26 of the third party administrator. File transfer server 38 may authenticate the system, receive the file, review file for format requirements, and submit the eligibility file as a request to API gateway server 36, for example, as described in FIG. 8. API gateway server 36 may rely on authentication performed by file transfer server 38 and forward the file to message broker 42. Message broker 42 queues the file for file transfer micro service 44d and sends when micro service 44d becomes available.

Micro service 44d processes the file to create records for the new member. In processing the file, micro service 44d sends a number of messages to portfolio management micro service 44a via message broker 42 to prompt portfolio management micro service 44a to create records for the new member. In processing the messages, portfolio management micro service 44a sends one or more messages to data access micro service 44b, via messages broker 42, to request data be added to data servers 50.

In processing the file, micro service 44d also sends a number of messages using message broker 42 to business management micro service 44d (or third party software platform) to provision a new smart card 16 for the member, send a welcome email to the new member, and/or mail new member documents to the new member's address along with the smart card 16. In the email and/or new member documents, the member is invited to use a web portal for members (provided by front end server 24) to activate the new card.

When the member logs into the member portal, front end server 24 provides log in information to API gateway server 36. API gateway server 36, authenticates the user with authentication server 34. Upon successful authentication, API gateway server 36 provides an authentication token to front end system for use to authenticate subsequent messages that are send to API gateway server 36 to request actions requested by user via the member portal.

After logging in, the web portal may prompt the new member to accepting terms and conditions; provide a profile picture; set up multi-factor authentication for the member and adult dependents; providing voluntary medical history; providing medication history; providing allergies and emergency contact information and/or set up preferences. In response to the member providing information, front end server 24 sends one or more messages to API gateway server to request the information by added to back end system 30. The previously provided authentication token is include in the message sent to the API gateway server 36. The API gateway server 36 uses the token to authenticate the message with authentication server 34. In response to successfully authenticating the message, API gateway server 36 forwards the message to messages broker 42. Message broker queues the message for processing by portfolio management micro service 44a and sends the messages when portfolio management micro service 44a is available. In processing the messages, portfolio management micro service 44a sends one or more messages to data access micro service 44b, via messages broker 42, to request data be added to data servers 50.

ALTERNATIVE ARRANGEMENT(S)

With reference to FIGS. 12-17, various additional features and alternatives of system 10 are presented. Some components of the system presented in FIGS. 12-17 are similar to components of the system 10 presented in FIGS. 1-11 and therefore all of the teaching presented herein with respect to FIGS. 1-11 applies equally to and is incorporated into the teaching presented in FIGS. 12-17 unless specifically stated otherwise.

Front End System 12:

In one or more arrangements, system 10 includes a front end system 12. Front end system 12 is formed of any suitable design, arrangement, and circuitry and is configured to facilitate storage, processing, or access to data in back end system 30 by end users. In the arrangement shown in FIG. 12, as one example, front end system 12 includes a number of front end servers 20 (e.g., implemented on reader devices 146 and/or partner systems 26), a card reader 14, and a smart card 16, among other components.

Reader Device 146:

In one or more arrangements, system includes reader device 146 configured to facilitate emergency access to patient records by emergency medical technicians and other medical providers. Reader device 146 is formed of any suitable design, arrangement, and circuitry and is configured to authenticate the device with back end systems 30 using credentials on a smart card 16 of a patient and to provide access to medical data of the patient once authenticated. In one or more arrangements, as some non-limiting examples, reader device 146 may be a mobile device such as a smart phone, tablet, laptop, or personal digital assistant, a desktop computer, and/or any other computing device. In one arrangement shown, as one example, reader device 146 has a housing 148, a control circuit 150, a communication module 158, a display 168, at least one input 170, and a power source 174.

Housing 148:

In the arrangement shown, as one example, reader device 146 includes a housing 148. Housing 148 is formed of any suitable size, shape and design and is configured provide the exterior shell of reader device 146. In one arrangement shown, as one example, housing 148 is a generally elongated member that is longer than it is wide, and it is wider than it is deep and in this way housing 148 fits well within the hand of a user. Housing 148 houses and holds and protects the other components of reader device 146.

Control Circuit 150:

Control circuit 150 is formed of any suitable size, shape, design, technology, and in any arrangement and is configured to control operation of other components of reader device 146 to facilitate authentication of a patient's smart card 16 and retrieval of the patient's medical records from back end system 30. In the arrangement shown, as one example implementation, reader device 146 includes control circuit 150 that includes a processing circuit 152 and memory 154 having software code or instructions that facilitates the computational operation of reader device 146. Processing circuit 152 may be any computing device that receives and processes information and outputs commands according to software code or instructions stored in memory 154. Memory 154 may be any form of information storage such as flash memory, ram memory, dram memory, a hard drive, or any other form of memory. Processing circuit 152 and memory 154 may be formed of a single combined unit. Alternatively, processing circuit 152 and memory 154 may be formed of separate but electrically connected components. Alternatively, processing circuit 152 and memory 154 may each be formed of multiple separate but electrically connected components.

Software code or instructions is any form of information or rules that provides guidance as to how processing circuit 152 is to receive, interpret and respond to information. Software code or instructions is stored in memory 154 and accessible to processing circuit 152. As an illustrative example, in one or more arrangements, software code or instructions may configure processing circuit 152 of reader device 146 to perform the following steps: 1) discover smart card 16; 2) attempt to authenticate smart card 16 with back end system 30; 3) in response to successfully authenticating smart card 16, retrieving patient information from a data server 50 of back end system 30; and 4) displaying retrieved patient information.

Communication Module 158:

Communication module 158 is formed of any suitable size, shape, design, technology, and is formed in any arrangement and is configured to facilitate communication with smart card 16 and back end system 30. In the arrangement shown, as one example, communication module 158 includes a first communication circuit 160 configured to communicate with smart card 16 and a second communication circuit 162 configured to communicate with back end system 30. The communication circuits 160/162 are formed of any suitable size, shape, design, technology, and is formed in any arrangement and are configured to facilitate communication with smart card 16 and back end system 30. In this example arrangement, first communication circuit 160 is configured to wirelessly communicate with smart card 16 using near field communication and second communication circuit 162 is configured to communicate with back end system 30 via one or more communication networks (e.g., the internet). In one or more arrangements, as one example, each of the communication circuits 160/162 has a respective transceiver (not shown) and an antenna (not shown). A transceiver is any electronic device that facilitates two-way communication, that is, the delivery of information from reader device 146 to other components of the system 10 as well as the reception of information from other components of the system 10 to reader device 146. An antenna is any device that is configured to receive wireless signals from over-the-air communication and/or transmit wireless signals in over-the-air communication. In an example arrangement, a transceiver of a communication circuit 160/162 is connected with a respective antenna, which may be a monopole antenna, dipole antenna, a loop antenna, a fractal antenna, or any other form of an antenna, to facilitate transmission and/or reception of signals in the form of electromagnetic radio frequencies.

It is contemplated that in various arrangements, the communication circuits 160/162 may be configured to communicate using various wired and/or wireless communication technologies and protocols over various networks including but not limited to, for example, RFID, Near Field Communication (NFC), 802.11/Wi-Fi, Wi-Max, Bluetooth, Bluetooth low energy, UltraWideband (UWB), 802.15.4/ZigBee, ZWave, GSM/EDGE, UMTS/HSPA+/HSDPA, CDMA, LTE, FM/VHF/UHF networks, and/or any other communication protocol, technology or network.

Display 168:

Display 168 is formed of any suitable size, shape, design, technology, and is formed in any arrangement and is configured to facilitate display of graphical user interface and/or patient medical records. In one or more arrangements, display 168 may be, for example, a screen or monitor of a computing device, tablet, and/or smartphone.

Input(s) 170:

In the arrangement shown, as one example, reader device 146 includes at least one input 170. Inputs 170 are formed of any suitable size, shape and design and are configured to facilitate data and/or control commands to be entered by an operator into reader device 146. In the arrangement shown, as one example, the at least one input 170 includes a plurality of buttons that are pressed by an operator.

In an alternative arrangement, as one example, at least one input 170 and display 168 are combined as a touch screen display that facilitates the entry of information by interaction with a touch screen and facilitate display of a graphical user interface and/or patient medical records. In another alternative arrangement, as one example, the at least one input 170 is a keyboard, mouse and/or GUI (graphical user interface). In an alternative arrangement, as one example, the at least one input 170 is a joystick, a roller ball, a knob, or any other form of an input. Additionally or alternatively, in one or more arrangements, the at least one input 170 and/or display may be implemented on a separate device that is communicatively connected to reader device 146. Any other form or arrangement of an input 170 and display 168 is hereby contemplated for use.

Power Source 174:

In the arrangement shown, as one example, reader device 146 includes a power source 174. Power source 174 is formed of any suitable size, shape and design and is configured to provide power to reader device 146 so as to facilitate the operation of the electrical components of the reader device 146. In the arrangement shown, as one example, power source 174 is formed of one or more batteries, which may or may not be rechargeable. Additionally or alternatively, in one or more arrangements, power source 174 may include a solar cell or solar panel or similar technology that may power or recharge reader device 146. Additionally or alternatively, in one or more arrangements, power source 174 may be line-power that is power that is delivered from an external power source into the reader device 146 through a wired connection. Any other form of a power source 174 is hereby contemplated for use.

Not Limited to any Particular System or Device:

In various embodiments, reader device 146 may be implemented using various different devices and/or systems to facilitate emergency access to patient medial data by medical providers in different applications. As an illustrative example, in one or more arrangements, reader device 146 may be a mobile device (such as a smartphone or tablet) carried by a medical provider (such as an emergency room doctor or emergency medical technician (EMT)). As another illustrative example, in one or more arrangements, reader device 146 may be an on vehicle computing system built into an ambulance. As yet another illustrative example, in one or more arrangements, reader device 146 may be implemented by application program interface software 28 installed on a partner system alongside partner software 26. Reader device 146 may be any other form of an electronic device.

In these examples, a mobile app 22 or web app 24, API 28 or other software on the reader device 146 is configured to communicate with smart card 16 and back end system 30 to authenticate the smart card 16 and retrieve medical records for a patient associated with the smart card 16 from a data server 50 of back end system 30 for use by medical providers. In some various arrangements, reader device 146 is configured to display medical records to medical providers directly (e.g., on display 168). Additionally or alternatively, in some various arrangements, reader device 146 is configured to provide retrieved medical records to partner software 26 for display to medical providers using the partner software.

Figure 15:
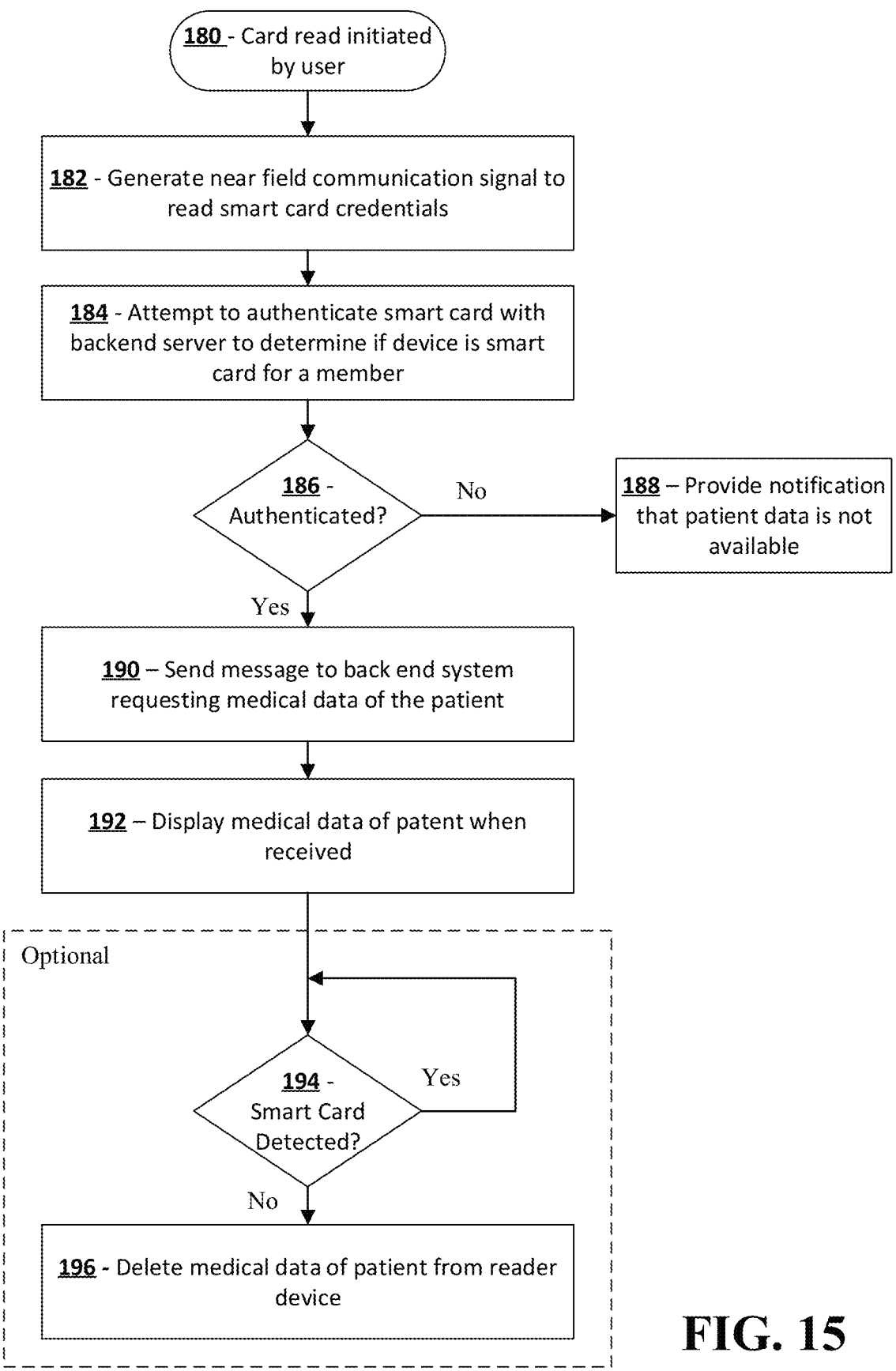
FIG. 15 shows an example process that may be performed by reader device to a provide medical provider access to patient medical records, consistent with one or more embodiments.

Manual Read of Smart Card:

In various arrangements, reader device 146 may utilize various different processes to retrieve and display patient medical record to medical providers. FIG. 15 shows an example process that may be performed by reader device 146 to provide medical providers access to patient medical records. In this example, the process is manually initiated by a user at process start 180. Once initiated, reader device 146 generates a near field communication signal at process block 182 to read credentials of smart card 16. At process block 184, reader device 146 attempts to authenticate the smart card 16 with back end system 30. If the smart card 16 cannot be authenticated at decision block 186, the reader device 146 provides a notification to the medical provider that patient data is not available at process block 188.

Otherwise, the process proceeds from decision block 186 to process block 190, where reader device 146 sends a message to back end system 30 requesting medical records of the patient associated with the smart card 16. In response to the message, back end system 30 retrieves the medical records as previously described with reference to FIGS. 1-11. At process block 192, once medical records are received by reader device 146 from back end system 30, the reader device 146 displays medical data of the patient for use in treatment by a medical provider.

Automated Deletion of Medical Records After Treatment:

Optionally, in one or more arrangements, reader device 146 is configured to automatically delete medical records after treatment is completed to ensure compliance with provider policies and/or relevant regulations relating to access and/or storage of patient data. In the example process shown in FIG. 15, as one example, after medical data of the patient is displayed at process block 192, the process loops at decision block 194, while the smart card 16 is still detected (e.g., via NFC) by reader device 146. Once smart card 16 is no longer detected, the process proceeds to process block 196, where reader device 146 deletes the medical data of the patient from the reader device 146. Additionally or alternatively, in one or more arrangements, reader device 146 may be configured to delete the medical data of the patient from the reader device 146 when a user exits mobile app 22 or web app 24. Additionally or alternatively, in one or more arrangements, reader device 146 may be configured to delete the medical data of the patient from the reader device 146 after a predetermined period of time specified in a configuration file of reader device 146.

Automated Scan for and Read of Smart Card:

In one or more arrangements, reader device 146 or other front end server 20 (e.g., 22, 24, and/or 26) may be configured to operate on a continuous scanning mode, in which, reader device 146 scans for smart cards that are associated with a patient account stored in back end system 30.

Figure 16:
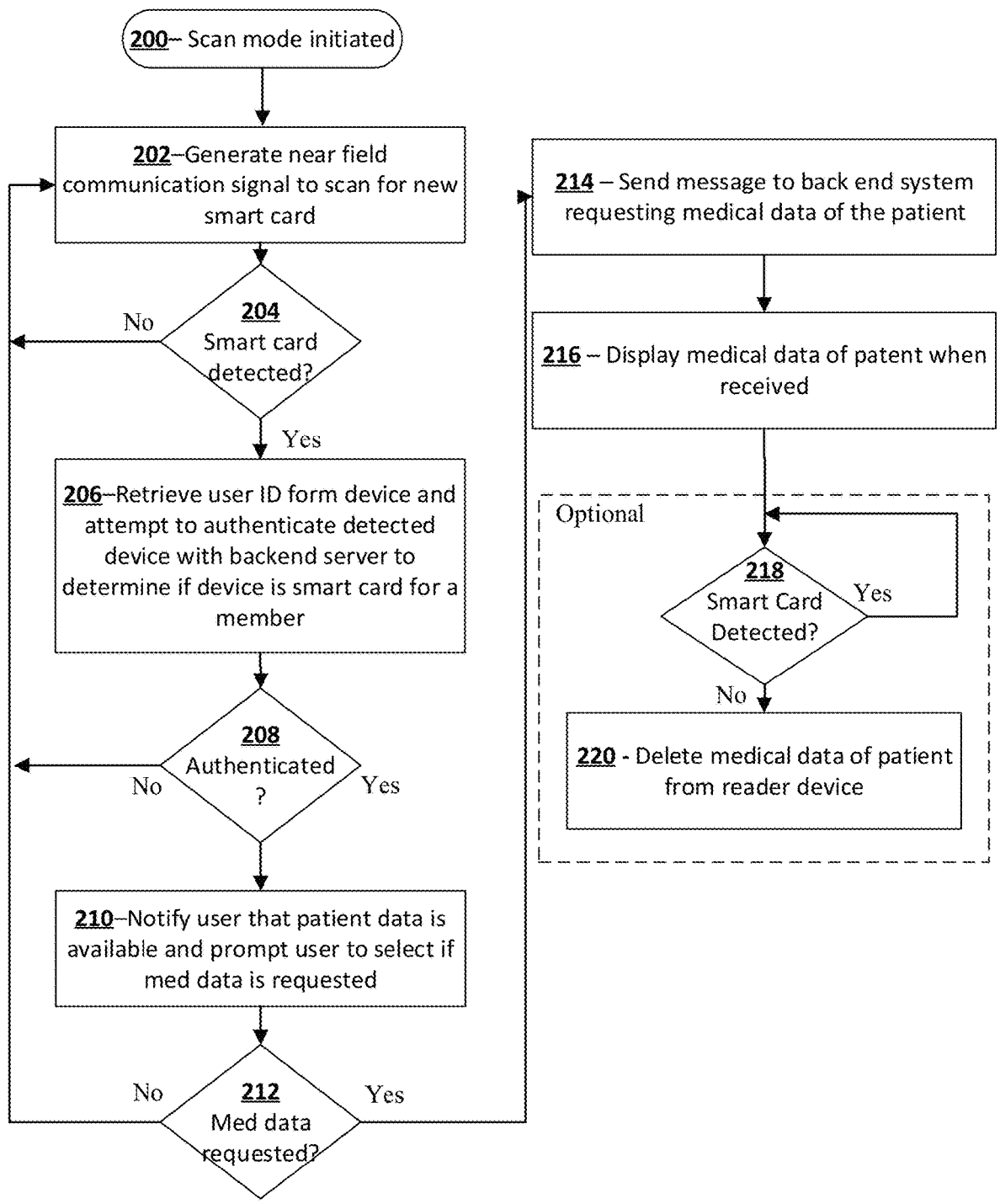
FIG. 16 shows another example process that may be performed by reader device to provide medical providers access to patient medical records, consistent with one or more embodiments.

FIG. 16 shows an example process that may be performed by reader device 146 to provide medical providers access to patient medical records. In this example, the process continuously scans for smart cards 16 once the process is initiated at process start 200. Once initiated, reader device 146 generates a near field communication signal at process block 202 to scan for new smart cards 16. The process loops at decision block 204 until a new smart card 16 is detected. One a smart card 16 is detected the process proceeds to process block 206. At process block 206, reader device 146 attempts to authenticate the smart card 16 with back end system 30. If the smart card 16 cannot be authenticated at decision block 208, the process returns to process block 202 where reader device 146 continues scanning for new smart cards 16. Otherwise, if the smart card 16 is successfully authenticated at decision block 208, the process proceeds to process block 210.

At process block 210, reader device 146 provides a notification to the medical provider that patient data is available and prompts the medical provider to select whether they would like to retrieve the medical data. In this example arrangement, since the medical provider is not alerted/prompted unless the smart card 16 is authenticated with back end system 30, no efforts or actions are required by the medical technician unless the patient is in the system 10. In this manner, the medical provider does not waste precious time and effort attempting to search for and/or scan smart cards 16 for patients that are not in the system 10. Rather, the medical provider can focus on providing medical treatment to the patient.

Prompting the medical provider to affirmatively select to retrieve the medical data may help to avoid unnecessary access to patient medical data. However, embodiments are not so limited. Rather, it is contemplated that, in one or more arrangements, reader device may be configured to automatically retrieve medical data of a patient if smart card 16 is successfully authenticated.

If the medical provider selects not to retrieve the medical data of the patient, the process returns from decision block 212 to process block 202, where reader device 146 continues to scan for new smart cards 16. Otherwise, if the medical provider selects not to retrieve the medical data of the patient, the process continues from decision block 212 to process block 214.

At process block 214, reader device 146 sends a message to back end system 30 requesting medical records of the patient associated with the smart card 16. In response to the message, back end system 30 retrieves the medical records as previously described with reference to FIGS. 1-11. At process block 216, once medical records are received by reader device 146 from back end system 30, the reader device 146 displays medical data of the patient for use in treatment by a medical provider.

Automated Deletion of Medical Records After Treatment:
Optionally, in one or more arrangements, reader device 146 is configured to automatically delete medical records after treatment is completed to ensure compliance with provider policies and/or relevant regulations relating to access and/or storage of patient data. In the example process shown in FIG. 16, as one example, after medical data of the patient is displayed at process block 216, the process loops at decision block 218, while the smart card 16 is still detected (e.g., via NFC) by reader device 146. Once smart card 16 is no longer detected, the process proceeds to process block 220, where reader device 146 deletes the medical data of the patient from the reader device 146. Additionally or alternatively, in one or more arrangements, reader device 146 may be configured to delete the medical data of the patient from the reader device 146 when a user exits mobile app 22 or web app 24. Additionally or alternatively, in one or more arrangements, reader device 146 may be configured to delete the medical data of the patient from the reader device 146 after a predetermined period of time specified in a configuration file of reader device 146.

Figure 17:
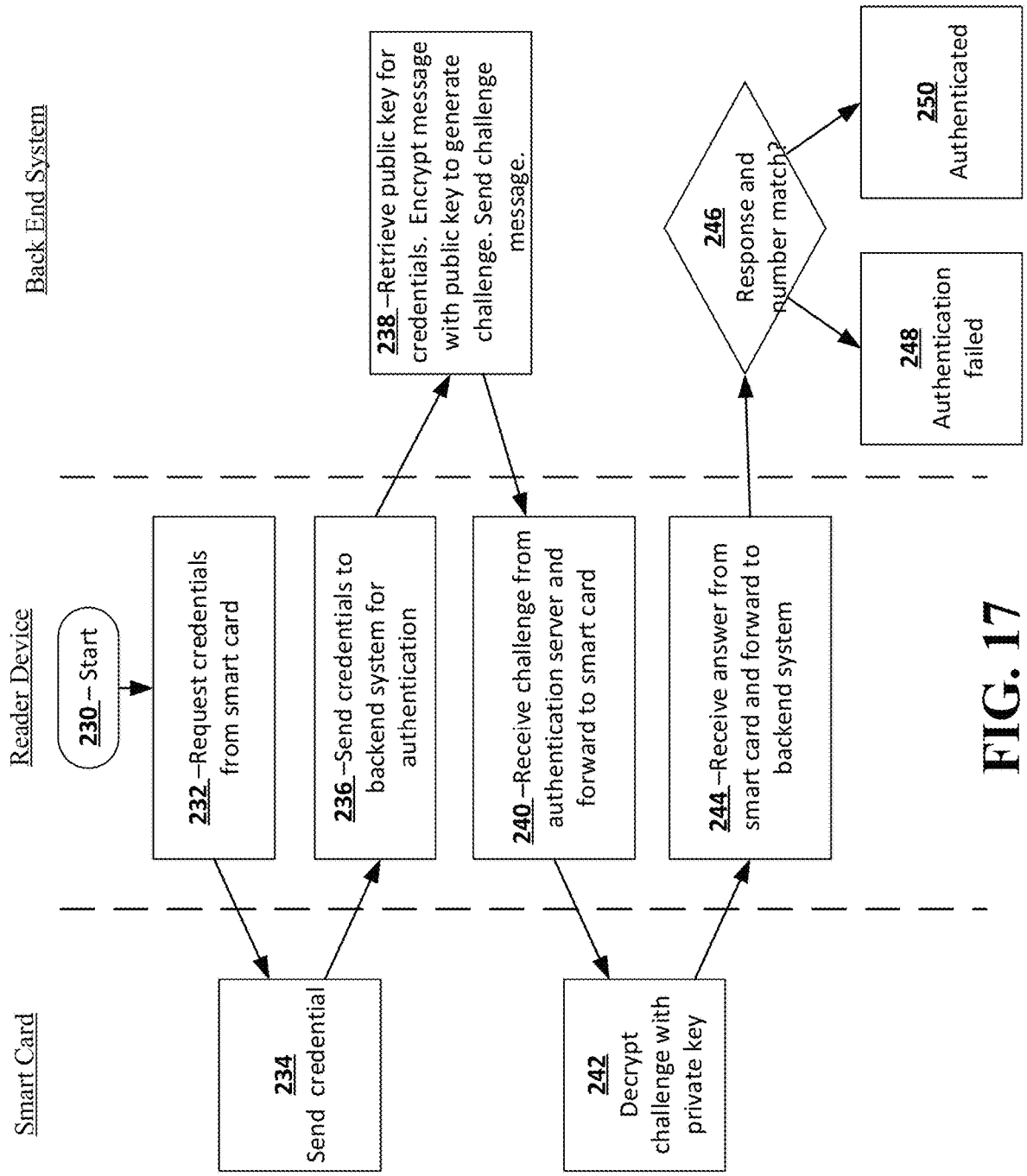
FIG. 17 shows one example process that may be performed by reader device to authenticate smart card with back end system, consistent with one or more embodiments.

Example Authentication Process:
In various arrangements, reader device 146 may utilize various different processes to authenticate smart card 16 with back end system 30. FIG. 17 shows one example process that may be performed by reader device 146 to authenticate smart card 16 with back end system 30 in accordance with one or more arrangements. In this example, the authentication process is initiated at process start 230. At process block 232, reader device 146 sends a communication to smart card 16 to request credentials from the smart card 16, which uniquely identify the smart card 16 and/or patient. In response, smart card 16 sends the credentials to the reader device 146 at process block 234. At block 236, reader device 146 sends the credentials to back end system 30 for authentication. In response to receiving the credential at process block 238, back end system 30 retrieves a public key for the credentials, encrypts a message with the public key to create a challenge message, and sends the challenge message to reader device 146. At process block 240, the reader device 146 receives the challenge message and forwards the challenge message to smart card 16. At block 242, the smart card decrypts the challenge message with a private key stored in the smart card to generate an answer and sends the answer to reader device 146. At process block 244, the reader device 146 receives and forwards the answer to back end system 30. The back end system 30 compares the answer to the original message. If the response and the answer match at decision block 246, back end system 30 determines the smart card 16 to be authenticated at process block 250. Otherwise, if the response and the answer do not match at decision block 246, back end system 30 determines that authentication of the smart card 16 has failed at process block 248. However, the embodiments are not so limited. Rather it is contemplated that smart card 16, reader device 146 and back end system 30 may utilize any other process or method for authentication, or multiple processes or methods for authentication.

Display Format of Medical Data of Patient:
In different arrangements and medical applications, reader device 146 may be configured to retrieve various different types of medical data and/or display retrieved data in various formats. As one example, in an example arrangement adapted for use by an emergency medical technician (EMT), reader device 146 may be configured to retrieve and display a summary of a patient's medical records that are of foremost importance to emergency medical treatment. Such a summary of information may include but is not limited to, for example, medical conditions and/or complications, known allergies, blood type, current prescriptions, primary doctors and/or specialist doctors of patient and contact information thereof.

As another example, in an example arrangement adapted for use by a doctor in a hospital, reader device 146 may be configured to retrieve a full medical history of a patient. In various different arrangements, reader device 146 may provide various graphical user interfaces (GUI) to organize and display the full medical history of a patient. In one or more arrangements, the GUI provided by reader device 146 may organize medical data of a patient into a series of tabs. For example, the GUI may provide a first tab window that displays the summary of the patient's medical records and one or more additional tab windows that display the full medical history of a patient.

Various blocks, modules, or other circuits may be implemented to carry out one or more of the operations and activities described herein and/or shown in the figures. In these contexts, a "block" (also sometimes "logic circuit", "control circuit," "processing circuit," "server," "module," or "system") is a circuit specifically configured and arranged to carry out one or more of these or related operations/activities. For example, such circuits may be discreet logic circuits or programmable logic circuits configured and arranged for implementing these operations/activities, as shown in the figures and/or described in the specification. In certain embodiments, such a programmable circuit may include one or more programmable integrated circuits (e.g., field programmable gate arrays and/or programmable ICs). Additionally or alternatively, such a programmable circuit may include one or more processing circuits (e.g., a computer, microcontroller, system-on-chip, smart phone, server, and/or cloud computing resources). For instance, computer processing circuits may be programmed to execute a set (or sets) of instructions (and/or configuration data). The instructions (and/or configuration data) can be in the form of firmware or software stored in and accessible from a memory (circuit). Certain aspects are directed to a computer program product (e.g., nonvolatile memory device), which includes a machine or computer-readable medium having stored thereon instructions which may be executed by a computer (or other electronic device) to perform these operations/activities.

In various implementations, disclosed blocks, modules, or other circuits, and/or devices may be communicatively connected using any number of communication protocols over various data networks and/or data buses, which may include but are not limited to, for example, NFC/RFID, 802.3, 802.11/Wi-Fi, Wi-Max, GSM/EDGE, UMTS/HSPA+/HSDPA, CDMA, LTE, Bluetooth, Bluetooth Low Energy, UltraWideband (UWB), ZigBee, Zwave, and/or FM/VHF/UHF networks, PCI, PCIe, SCSI, USB, Hypertransport, or any other communication medium and/or protocol.

From the above discussion it will be appreciated that the system 10 improves upon the state of the art. For example, some various embodiments provide an improved system for storing, processing, and assessing data related to medical services: that is interoperable with third party systems; that facilitates transparency, security and verifiability of data; that improves efficiency in storage and processing of data and transactions; that utilizes a smart card to facilitate identification, authentication, and approvals; that is strong, robust, durable, and fault tolerant; that can be used in many applications; that provides unique functionality; that facilitates fast processing of data and transactions; that is scalable; that is distributed; that is easy and intuitive to use; that saves time; and/or that improves a user experience.

It will be appreciated by those skilled in the art that other various modifications could be made to the device without parting from the spirit and scope of this disclosure. All such modifications and changes fall within the scope of the claims and are intended to be covered thereby.

What is claimed:

1. A system for storage, processing, and accessing of data, comprising:
   a front end system, the front end system including one or more front end servers;
   wherein the one or more front end servers are configured to provide a first user interface configured to provide a healthcare provider access to medical and drug history data for a patient when authorized;
   wherein the one or more front end servers are configured to provide a second user interface configured to permit the patient to set permissions for access to medical and drug history data for the patient by healthcare providers;
   the patient having a smart card;
   a back end system communicatively connected to the front end system;
   wherein the back end system includes one or more data servers;
   wherein the one or more data servers store the medical and drug history data for the patient;
   wherein in response to scanning the smart card of the patient via a card reader, the front end system is configured to authenticate the patient and the healthcare provider;
   wherein in response to successful authentication of the patient and the healthcare provider using the smart card of the patient, the healthcare provider is permitted access, via the first user interface, to medical and drug history data in the one or more data servers for the patient that is specified by the set permissions as being accessible by healthcare providers that are successfully authenticated;
   wherein the back end system is configured to deny the healthcare provider access to any medical and drug history data in the one or more data servers for the patient that is specified by the set permissions as being inaccessible by healthcare providers;
   wherein the back end system is configured to deny the healthcare provider access to any medical and drug history data in the one or more data servers for the patient if the healthcare provider is authenticated without the smart card of the patient.

2. The system of claim 1, wherein upon successful authentication, the front end system is further configured to retrieve information of a health insurance policy of the patient.

3. The system of claim 1, wherein upon successful authentication, the front end system is further configured to verify validity of a health insurance policy of the patient.

4. The system of claim 1, wherein in authenticating the patient using the smart card, the first user interface prompts the patient to enter a personal identification number, wherein the back end system is configured to authenticate the patient using the smart card and the personal identification number.

5. The system of claim 1, wherein the first user interface is further configured to facilitate submission of pre-approval requests for procedures to be provided to the patient.

6. The system of claim 1, wherein the system is configured to permit the patient to use the smart card for payment of medical services provided to the patient by scanning the smart card with the card reader;
   wherein in response to the patient scanning the smart card for payment, the system is configured to debit payment from a healthcare savings account, bank account, or other payment system linked to the smart card in the one or more data servers.

7. A system for accessing medical data of a patient, comprising:
   a front end system;
   the front end system providing a user interface;
   the front end system including a reader device;
   the reader device configured to wirelessly communicate with a smart card of the patient;
   a back end system;
   the back end system communicatively connected to the front end system;
   wherein the back end system includes one or more data servers;
   wherein the one or more data servers store the medical data of the patient;
   wherein the one or more data servers store permissions for access to medical and drug history data for the patient by healthcare providers;
   wherein the reader device is configured to communicate with the smart card and back end system;

wherein the reader device is configured to authenticate the patient and the healthcare provider with the back end system using data received from the smart card;

wherein the authentication of the healthcare provider using the data received from the smart card indicates to the back end system that the patient has authorized the healthcare provider to access medical data of the patient;

wherein in response to successful authentication of the patient and the healthcare provider using the smart card of the patient, the healthcare provider is permitted access, via the user interface, to medical and drug history data for the patient in the one or more data servers;

wherein the back end system is configured to deny the healthcare provider access to any medical and drug history data in the one or more data servers for the patient that is specified by the permissions as being inaccessible by healthcare providers;

wherein the back end system is configured to deny the healthcare provider access to any medical and drug history data in the one or more data servers for the patient if the healthcare provider is authenticated without the smart card of the patient.

8. The system of claim 7, wherein the reader device is a smart phone.

9. The system of claim 7, wherein the reader device is a desktop computer.

10. The system of claim 7, wherein the reader device is configured to communicate with the smart card using near field communication.

11. The system of claim 7, wherein the reader device is configured to communicate with the smart card and back end system to authenticate the smart card with the back end system in response to input from the healthcare provider.

12. The system of claim 7, wherein the reader device is configured to automatically scan for smart cards, and in response to detecting the presence of the smart card, communicate with the smart card and back end system to authenticate the smart card with the back end system.

13. The system of claim 7, wherein the reader device is configured to, after displaying medical data of the patient, automatically delete the medical data of the patient from the reader device once the smart card is no longer detected by the reader device.

14. The system of claim 7, wherein the reader device is configured to, after displaying medical data of the patient, automatically delete the medical data of the patient from the reader device after a predetermined period of time specified in a configuration file of the reader device.

15. The system of claim 7, wherein the back end system includes one or more interface servers; and
   wherein the one or more interface servers are configured to operate as a gateway between the front end system, and the one or more data servers.

16. The system of claim 7, wherein the reader device includes:
   a control circuit;
   a communication module;
   a display;
   one or more inputs;
   a power source;
   the power source configured to power the control circuit, communication module, and display;
   wherein in response to input via the one or more inputs, the control circuit causes the communication module to communicate with the smart card and the back end system to authenticate the smart card with the back end system;
   wherein in response to authenticating the smart card with the back end system, the control circuit causes the communication module to send messages to retrieve the medical data of the patient from the back end system;
   wherein in response to retrieving the medical data of the patient from the back end system the control circuit causes the display to display the medical data of the patient.

17. A system for providing accessing to medical data of a patient having a smart card, comprising:
   a front end system;
   the front end system including a reader device;
   a back end system;
   the back end system communicatively connected to the front end system;
   wherein the back end system includes a first data server;
   wherein the first data server stores the medical data of the patient;
   wherein the reader device is configured to authenticate the patient and a medical provider with the back end system using data received from the smart card of the patient;
   wherein the front end system is provided an authentication token in response to successful authentication of the patient and the medical provider using the data received from the smart card or the patient;
   wherein in response to user input the front end system is configured to retrieve the medical data of the patient by communicating a request to the back end system;
   wherein the request includes the authentication token and specifies the medical data to be retrieved;
   wherein the authentication token indicates if the back end system that the medical provider was authenticated using the smart card of the patient;
   wherein in response to the authentication token of the request indicating that the medical provider was authenticated using the smart card of the patient, the medical provider is permitted access to the medical data specified in the request;
   wherein in response to the authentication token of the request indicating that the medical provider was not authenticated using the smart card of the patient, the medical provider is denied access to the medical data of the patient.

* * * * *